(12) United States Patent
Rhoads

(10) Patent No.: US 6,525,245 B1
(45) Date of Patent: Feb. 25, 2003

(54) METHOD FOR IDENTIFYING COMPONENTS INVOLVED IN SIGNAL TRANSDUCTION PATHWAYS IN HIGHER PLANTS

(75) Inventor: David M. Rhoads, Scottsdale, AZ (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 09/577,424

(22) Filed: May 22, 2000

Related U.S. Application Data
(60) Provisional application No. 60/136,145, filed on May 20, 1999.

(51) Int. Cl.$^7$ .............................. A01H 1/06; A01H 5/00; C12N 15/82; C12N 15/12; C12N 15/84; C12N 15/01; C12N 15/31
(52) U.S. Cl. ...................... 800/278; 800/276; 800/287; 800/288; 800/282; 800/291; 800/294; 800/298; 800/306; 435/320.1; 435/419; 435/4; 435/8; 435/468; 435/469; 435/441
(58) Field of Search ................................. 800/276, 278, 800/287, 288, 291, 294, 298, 317.3, 282, 306; 536/23.2, 24.1; 435/320.1, 419, 414, 4, 468, 469, 441, 8

(56) References Cited

U.S. PATENT DOCUMENTS
5,670,356 A * 9/1997 Sherf et al. .................. 435/189

OTHER PUBLICATIONS

Hill, M. A. and Preiss, J. "Functional Analysis of Conserved Histidines in ADP–Glucose Pyrophosphorylase from *Escherichia coli*." 1998, Biochemical and Biophysical Res. Comm., vol. 244, pp. 573–577.*
Broun, P. et al, "Catalytic Plasticity of Fatty Acid Modification Enzymes Underlying Chemical Diversity of Plant Lipids." 1998, Science, vol. 282, pp. 1315–1317.*
Bowie, J. U. et al., "Deciphering the Message in Protein Sequences: Tolerance to Amino Acid Substitutions." 1990, Science, vol. 247, pp. 1306–1310.*
Lazar, E. et al., "Transforming Growth Factor a: Mutation of Aspartic Acid 47 and Leucine 48 Results in Different Biological Activities." 1988, Molecular and Cellular Biology, vol. 8, pp. 1247–1252.*
Barnes, W. M. "Variable patterns of expression of luciferase in transgenic tobacco leaves." 1990, Proc. Natl. Acad. Sci. USA, vol. 87, pp. 9183–9187.*
Feldman, K. A. et al., "Mutagenesis in Arabidopsis, in Arabidopsis, ed by Meyerwitz et al. " 1994, Cold Spring Harbor Press, pp. 137–172.*
Vanlerberghe, G. C. and McIntosh, L. "Alternative Oxidase: From Gene to Function." 1997, Annu. Rev. Plant Physiol. Plant Mol. Biol. , vol. 48, pp. 703–734.*

Susek, R. E. et al., "Signal Transduction Mutants of Arabidopsis Uncouple Nuclear CAB and RBCS Expression from Chloroplast Development." 1993, Cell, vol. 74, pp. 787–799.*
Van Oosten, J. M. et al., "An Arabidopsis mutant showing reduced feedback inhibition of photosynthesis." 1997, The Plant Journal, vol. 12, pp. 1011–1020.*
Ishitani, M. et al., "Genetic Analysis of Osmotic and Cold Stress Signal Transduction in Arabidopsis: Interactions and Convergence of Abscisic Acid–Dependent and Abscisic Acid–Independent Pathways." 1997, The Plant Cell, vol. 9, pp. 1935–1949.*
Donald, R. G. K. and Cashmore, A. R. "Mutation of either G box or I box sequences profoundly affects expression from the Arabidopsis rbcS–1A promoter." 1990, The EMBO Journal vol. 9, pp. 1717–1726.*
Ow, D. W. et al., "Transient and Stable Expression of the Firefly Luciferase Gene in Plant Cells and Transgenic Plants." 1986, Science, vol. 234, pp. 856–859.*
Millar, et al. "A Novel Circadian Phenotype Based on Firefly Luciferase Expression in Transgenic Plants." Plant Cell, US, American Society of Plant Physiologist, Rockville, MD, vol. 4, No. 9, 1992, pp. 1075–1087.
Database EM_PL Online, EMBL; Arabiodopsis thaliana genoic DNA, 1999, Database accession No. AB022215, XP002159114, abstract Nakamura Y: "Structural analysis of *Arabidopsis thaliana* chromosome 3. Sequence features of the regions of 4,504,864 bp covered by sixty P1 and TAC" DNA Res., 2000, pp. 131–135.
Aubert et al., Induction of Alternative Oxidase Synthesis by Herbicides Inhibiting Branched–Chain Amino Acid Synthesis, (1997), *The Plant Journal*, 11(4):649–657.
DeRisi et al., Exploring the Metabolic and Genetic Control of Gene Expression on a Genomic Scale, (1997), *Science* 278:680–686.
Elthon et al., Identification of the Alternative Terminal Oxidase of Higher Plant Mitochondria, (1987), *Proc. Natl. Acad. Sci. USA*, 84:8399–8403.
Elthon et al., Monoclonal Antibodies to the Alternative Oxidase of Higher Plant Mitochondria, (1989), *Plant Physiol*, 89:1311–1317.

(List continued on next page.)

*Primary Examiner*—David T. Fox
*Assistant Examiner*—Anne Kubelik

(57) ABSTRACT

The present invention relates to methods for determining nucleic acid sequences that encode components of signal transduction pathways in higher plants. The method comprises combining a portion of an AOX promoter linked in operable fashion to a reporter gene to detect nucleic acid sequences of components of the signal transduction pathways between mitochondria function and metabolic status and nuclear gene expression and the signal transduction pathways between branched chain amino acid biosynthetic pathways and nuclear gene expression. A polynucleotide that encodes a portion of an AOX promoter, AOX1a, operably linked to a luciferase reporter gene is provided. A recombinant vector, transformed cells, and transformed organisms containing this polynucleotide are disclosed.

42 Claims, 6 Drawing Sheets

OTHER PUBLICATIONS

Elthon et al., Mitochondrial Events During Development of Thermogenesis in *Sauromatum Guttatum* (Schott), (1989), *Planta,* 180:82–89.

Finnegan et al., Analysis of the Antimycin A–Inducible Promoter Region of Soybean GmAOXI, (1998), *Plant Mitochondria: From Gene to Function,* pp. 449–453.

Ishitani et al., HISO, A Genetic Locus Involved in Cold-Responsive Gene Expression in Arabidopsis, (1998), *The Plant Cell,* 10:1151–1161.

Kwast et al., Oxygen Sensing in Yeast: Evidence for the Involvement of the Respiratory Chain in Regulating the Transcription of a Subset of Hypoxic Genes, (1999), *Proc. Natl. Acad. Sci. USA,* 96:5446–5451.

Liao et al., RTGI and RTG2: Two Yeast Genes Required for a Novel Path of Communication from Mitochondria to the Nucleus, (1993), *Cell,* 72:61–71.

Liu et al., A Transcriptional Switch in the Expression of Yeast Tricarboxylic Acid Cycle Genes in Response to a Reduction or Loss of Respiratory Function, (1999), *Molecular and Cellular Biology,* pp. 6720–6728.

Maxwell et al., The Alternative Oxidase Lowers Mitochondiral Reactive Oxygen Production in Plant Cells, (1999), *Proc. Natl. Acad. Sci. USA,* 96:8271–8276.

Millar et al., Circadian Clock Mutants in Arabidopsis Identified by Luciferase Imaging, (1995), *Science,* 267:1161–1166.

Minagawa et al., Possible Involvement of Superoxide Anion in the Induction of Cyanide–Resistant Respiration in *Hansenula Anomala,* (1992), 320(3):217–219.

Poyton et al., Crosstalk Between Nuclear and Mitochondrial Genomes, (1996), *Annu. Rev. Biochem.,* 65:563–607.

Purvis, A.C., Role of the Alternative Oxidase in Limiting Superoxide Production by Plant Mitochondria, (1997), *Physiologia Plantarum,* 100:165–170.

Rhoads et al., Salicylic Acid Regulation of Respiration in Higher Plants: Alternative Oxidase Expression, (1992), *The Plant Cell,* 4:1131–1139.

Rhoads et al., The Salicylic Acid–Inducible Alternative Oxidase Gene AOXI and Genes Encoding Pathogenesis–Related Proteins Share Regions of Sequence Similarity in Their Promoters, (1993), *Plant Molecular Biology,* 21:615–624.

Rhoads, et al., Cytochrome and Alternative Pathway Respiration in Tobacco, (1993), *Plant Physiol.,* 103:877–883.

Saisho et al., Characterization of the Gene Family for Alternative Oxidase from *Arabidopsis Thaliana,* (1997), *Plant Molecular Biology,* 35:585–596.

Small et al., Enzymatic and Metabolic Studies on Retrograde Regulation Mutants of Yeast, (1995), *Biochemistry,* 34:5569–5576.

Vanlerberghe et al., Mitochondrial Electron Transport Regulation of Nuclear Gene Expression, (1994), *Plant Physiol.,* 105:867–874.

Vanlerberghe et al., Alternative Oxidase Activity in Tobacco Leaf Mitochondria, (1995), *Plant Physiol.,* 109:353–361.

Vanlerberghe et al., Signals Regulating the Expression of the Nuclear Gene Encoding Alternative Oxidase of Plant Mitochondira, (1996), *Plant Physiol.,* 111:589–595.

Wagner et al., Energy Metabolism of *Petunia Hybrida* Cell Suspensions Growing in the Presence of Antimycin A, (1992), *Molecular, Biochemical and Physiological Aspects of Plant Respiration,* pp. 609–614.

Wagner, A.M., A Role for Active Oxygen Species as Second Messengers in the Induction of Alternative Oxidase Gene Expression in *Petunia Hybrida* Cells, (1995), *FEBS Letters 368,* pp. 339–342.

Xie et al., Salicylic Acid Induces Rapid Inhibition of Mitochondrial Electron Transport and Oxidative Phosphorylation in Tobacco Cells, (1999), *Plant Physiology,* 120:217–225.

Zitomer et al., Regulation of Gene Expression by Oxygen in *Saccharomyces Cerevisiae,* (1992), *Microbiological Reviews,* 56(1):1–11.

* cited by examiner

| Antimycin A conc. | | Seedling avg. FW |
|---|---|---|
| 0 uM |  | 2.3 mg |
| 100 uM |  | 2.2 mg |
| 1000 uM |  | 2.0 mg |

SEQUENCE LISTING

<160> NUMBER OF SEQ ID NOS: 6

<210> SEQ ID NO 1
<211> LENGTH: 12614
<212> TYPE: DNA
<213> ORGANISM: Bacterial Plasmid DNA - Plasmid pZP-ALE
<220> FEATURE:
<221> NAME/KEY: CDS
<222> LOCATION: (1665)..(3317)

<400> SEQUENCE: 1

```
ttgatcccga ggggaaccct gtggttggca tgcacataca aatggacgaa cggataaacc      60
ttttcacgcc cttttaaata tccgttattc aataaacgc tcttttctct taggtttacc      120
cgccaatata tcctgtcaaa cactgatagt ttaaactgaa ggcgggaaac gacaatctga     180
tccaagctca agctgctcta gcattcgcca ttcaggctgc gcaactgttg ggaagggcga     240
tcggtgcggg cctcttcgct attacgccag ctggcgaaag ggggatgtgc tgcaaggcga     300
ttaagttggg taacgccagg gttttcccag tcacgacgtt gtaaaacgac ggccagtgcc     360
aagcttgcat gcctgcaggt cgactctaga ggatccccca gcttgcatgc ctgcaggtcg     420
actctagagg atctgtccat taaacccac taaaatgaag taggcttgaa tccatcatat     480
ataaatgtta aattaatagg gctgggaaaa aaacgaaaa ccgaaaaacc gaaccgtacc     540
aaaccaaaac aaatggtttg gtttggttat ggttttgtat aaaaacccat ttggttgtaa     600
tttttattta agttttggtt taggtttggt ttgattaaaa accgtaaaac cgaacgtttc     660
ttttgttttt gatttaaatt aaaaataatt gtatatatat atatatataa tgttcatttg     720
ataacatgat atctatcaaa ctatcgaaaa acaaaacct aactgtaacc taaactaaaa     780
ttctatataa attacatgct gtcatttagg atttgagttt acaaattaga ttttgatttt     840 attttatgcat cacacttata atttttttg gtaaaacat gaaaaaaccg gaaccaaacc     900
ggaaccgatc cgaaccaaaa tacatatggt ttttaaatgg ttttaattttt ttaaaaccaa     960 aaactgtaaa accgttaaaa ccgaaccgta accaaaccga atttatatg gtttttatat     1020 ggttttactt ttcttaaaat cgaaaaaccg taaaacctaa aaccgaatca aaaccaaacc     1080
gaaaaactga acgtccaacc cttaaatata atgaaaatcg aatgaatttg tttgaaagaa     1140
tcgaacaaaa ttgacaataa aatctaatta ggactatttt cgtctaattt tgacttagtt     1200
gaaacagaat attagcaaaa atactaaaac accacacgc gtaataatac ccacacacga     1260
tatcattaaa tttgaccaat aagaatctag ctcttggcga ccacgcaagt atcttccatc     1320
ttgctctcca agaaaaatct acaccggctt taaatttaca taaacaccct cagtcaaaga     1380
aaagtcgtaa acatagtctc tctcatgacc acaagggtaa cacagtcatc ctaaatataa     1440
accacacaag aaaactgtta tactttatac acgtgtcata gtctcattac atctacgtga     1500
agagtttcga tcatcaaccg ttcgttttct tactatataa accttgctcg agacctgcgt     1560
gtgaagcgta taaagacgac aaagtaaacc aaaaaaaaaa agagttctcc tacaatttc     1620 ctaaattctt ggatttgaga tttcactttt tccgatttga aacc atg gaa gac gcc      1676
                                                 Met Glu Asp Ala
                                                   1 aaa aac ata aag aaa ggc ccg gcg cca ttc tat ccg ctg gaa gat gga      1724
Lys Asn Ile Lys Lys Gly Pro Ala Pro Phe Tyr Pro Leu Glu Asp Gly
  5              10                15                 20 acc gct gga gag caa ctg cat aag gct atg aag aga tac gcc ctg gtt     1772
Thr Ala Gly Glu Gln Leu His Lys Ala Met Lys Arg Tyr Ala Leu Val
```

-continued

|  | 25 | 30 | 35 |  |
|---|---|---|---|---|
| cct gga aca att gct ttt aca gat gca cat atc gag gtg gac atc act<br>Pro Gly Thr Ile Ala Phe Thr Asp Ala His Ile Glu Val Asp Ile Thr<br>40 45 50 | | | | 1820 |
| tac gct gag tac ttc gaa atg tcc gtt cgg ttg gca gaa gct atg aaa<br>Tyr Ala Glu Tyr Phe Glu Met Ser Val Arg Leu Ala Glu Ala Met Lys<br>55 60 65 | | | | 1868 |
| cga tat ggg ctg aat aca aat cac aga atc gtc gta tgc agt gaa aac<br>Arg Tyr Gly Leu Asn Thr Asn His Arg Ile Val Val Cys Ser Glu Asn<br>70 75 80 | | | | 1916 |
| tct ctt caa ttc ttt atg ccg gtg ttg ggc gcg tta ttt atc gga gtt<br>Ser Leu Gln Phe Phe Met Pro Val Leu Gly Ala Leu Phe Ile Gly Val<br>85 90 95 100 | | | | 1964 |
| gca gtt gcg ccc gcg aac gac att tat aat gaa cgt gaa ttg ctc aac<br>Ala Val Ala Pro Ala Asn Asp Ile Tyr Asn Glu Arg Glu Leu Leu Asn<br>105 110 115 | | | | 2012 |
| agt atg ggc att tcg cag cct acc gtg gtg ttc gtt tcc aaa aag ggg<br>Ser Met Gly Ile Ser Gln Pro Thr Val Val Phe Val Ser Lys Lys Gly<br>120 125 130 | | | | 2060 |
| ttg caa aaa att ttg aac gtg caa aaa aag ctc cca atc atc caa aaa<br>Leu Gln Lys Ile Leu Asn Val Gln Lys Lys Leu Pro Ile Ile Gln Lys<br>135 140 145 | | | | 2108 |
| att atc atc atg gat tct aaa acg gat tac cag gga ttt cag tcg atg<br>Ile Ile Ile Met Asp Ser Lys Thr Asp Tyr Gln Gly Phe Gln Ser Met<br>150 155 160 | | | | 2156 |
| tac acg ttc gtc aca tct cat cta cct ccc ggt ttt aat gaa tac gat<br>Tyr Thr Phe Val Thr Ser His Leu Pro Pro Gly Phe Asn Glu Tyr Asp<br>165 170 175 180 | | | | 2204 |
| ttt gtg cca gag tcc ttc gat agg gac aag aca att gca ctg atc atg<br>Phe Val Pro Glu Ser Phe Asp Arg Asp Lys Thr Ile Ala Leu Ile Met<br>185 190 195 | | | | 2252 |
| aac tcc tct gga tct act ggt ctg cct aaa ggt gtc gct ctg cct cat<br>Asn Ser Ser Gly Ser Thr Gly Leu Pro Lys Gly Val Ala Leu Pro His<br>200 205 210 | | | | 2300 |
| aga act gcc tgc gtg aga ttc tcg cat gcc aga gat cct att ttt ggc<br>Arg Thr Ala Cys Val Arg Phe Ser His Ala Arg Asp Pro Ile Phe Gly<br>215 220 225 | | | | 2348 |
| aat caa atc att ccg gat act gcg att tta agt gtt gtt cca ttc cat<br>Asn Gln Ile Ile Pro Asp Thr Ala Ile Leu Ser Val Val Pro Phe His<br>230 235 240 | | | | 2396 |
| cac ggt ttt gga atg ttt act aca ctc gga tat ttg ata tgt gga ttt<br>His Gly Phe Gly Met Phe Thr Thr Leu Gly Tyr Leu Ile Cys Gly Phe<br>245 250 255 260 | | | | 2444 |
| cga gtc gtc tta atg tat aga ttt gaa gaa gag ctg ttt ctg agg agc<br>Arg Val Val Leu Met Tyr Arg Phe Glu Glu Glu Leu Phe Leu Arg Ser<br>265 270 275 | | | | 2492 |
| ctt cag gat tac aag att caa agt gcg ctg ctg gtg cca acc cta ttc<br>Leu Gln Asp Tyr Lys Ile Gln Ser Ala Leu Leu Val Pro Thr Leu Phe<br>280 285 290 | | | | 2540 |
| tcc ttc ttc gcc aaa agc act ctg att gac aaa tac gat tta tct aat<br>Ser Phe Phe Ala Lys Ser Thr Leu Ile Asp Lys Tyr Asp Leu Ser Asn<br>295 300 305 | | | | 2588 |
| tta cac gaa att gct tct ggt ggc gct ccc ctc tct aag gaa gtc ggg<br>Leu His Glu Ile Ala Ser Gly Gly Ala Pro Leu Ser Lys Glu Val Gly<br>310 315 320 | | | | 2636 |
| gaa gcg gtt gcc aag agg ttc cat ctg cca ggt atc agg caa gga tat<br>Glu Ala Val Ala Lys Arg Phe His Leu Pro Gly Ile Arg Gln Gly Tyr<br>325 330 335 340 | | | | 2684 |
| ggg ctc act gag act aca tca gct att ctg att aca ccc gag ggg gat | | | | 2732 |

```
Gly Leu Thr Glu Thr Thr Ser Ala Ile Leu Ile Thr Pro Glu Gly Asp
                345                 350                 355 gat aaa ccg ggc gcg gtc ggt aaa gtt gtt cca ttt ttt gaa gcg aag    2780
Asp Lys Pro Gly Ala Val Gly Lys Val Val Pro Phe Phe Glu Ala Lys
        360                 365                 370 gtt gtg gat ctg gat acc ggg aaa acg ctg ggc gtt aat caa aga ggc    2828
Val Val Asp Leu Asp Thr Gly Lys Thr Leu Gly Val Asn Gln Arg Gly
    375                 380                 385 gaa ctg tgt gtg aga ggt cct atg att atg tcc ggt tat gta aac aat    2876
Glu Leu Cys Val Arg Gly Pro Met Ile Met Ser Gly Tyr Val Asn Asn
390                 395                 400 ccg gaa gcg acc aac gcc ttg att gac aag gat gga tgg cta cat tct    2924
Pro Glu Ala Thr Asn Ala Leu Ile Asp Lys Asp Gly Trp Leu His Ser
405                 410                 415                 420 gga gac ata gct tac tgg gac gaa gac gaa cac ttc ttc atc gtt gac    2972
Gly Asp Ile Ala Tyr Trp Asp Glu Asp Glu His Phe Phe Ile Val Asp
                425                 430                 435 cgc ctg aag tct ctg att aag tac aaa ggc tat cag gtg gct ccc gct    3020
Arg Leu Lys Ser Leu Ile Lys Tyr Lys Gly Tyr Gln Val Ala Pro Ala
                440                 445                 450 gaa ttg gaa tcc atc ttg ctc caa cac ccc aac atc ttc gac gca ggt    3068
Glu Leu Glu Ser Ile Leu Leu Gln His Pro Asn Ile Phe Asp Ala Gly
                455                 460                 465 gtc gca ggt ctt ccc gac gat gac gcc ggt gaa ctt ccc gcc gcc gtt    3116
Val Ala Gly Leu Pro Asp Asp Asp Ala Gly Glu Leu Pro Ala Ala Val
    470                 475                 480 gtt gtt ttg gag cac gga aag acg atg acg gaa aaa gag atc gtg gat    3164
Val Val Leu Glu His Gly Lys Thr Met Thr Glu Lys Glu Ile Val Asp
485                 490                 495                 500 tac gtc gcc agt caa gta aca acc gcg aaa aag ttg cgc gga gga gtt    3212
Tyr Val Ala Ser Gln Val Thr Thr Ala Lys Lys Leu Arg Gly Gly Val
                505                 510                 515 gtg ttt gtg gac gaa gta ccg aaa ggt ctt acc gga aaa ctc gac gca    3260
Val Phe Val Asp Glu Val Pro Lys Gly Leu Thr Gly Lys Leu Asp Ala
                520                 525                 530 aga aaa atc aga gag atc ctc ata aag gcc aag aag ggc gga aag atc    3308
Arg Lys Ile Arg Glu Ile Leu Ile Lys Ala Lys Lys Gly Gly Lys Ile
            535                 540                 545 gcc gtg taa ttctagagaa ttcaggcctg atcctctagc tagagctttc             3357
Ala Val
    550 gttcgtatca tcggtttcga caacgttcgt caagttcaat gcatcagttt cattgcgcac   3417 acaccagaat cctactgagt tcgagtatta tggcattggg aaaactgttt ttcttgtacc   3477 atttgttgtg cttgtaattt actgtgtttt ttattcggtt ttcgctatcg aactgtgaaa   3537 tggaaatgga tggagaagag ttaatgaatg atatggtcct tttgttcatt ctcaaattaa   3597 tattatttgt ttttctctt atttgttgtg tgttgaattt gaaattataa agatatatgca   3657 aacattttgt tttgagtaaa aatgtgtcaa atcgtggcct ctaatgaccg aagttaatat   3717 gaggagtaaa acacttgtag ttgtaccatt atgcttattc actaggcaac aaatatattt   3777 tcagacctag aaaagctgca aatgttactg aatacaagta tgtcctcttg tgttttagac   3837 atttatgaac tttcctttat gtaattttcc agaatccttg tcagattcta atcattgctt   3897 tataattata gttatactca tggatttgta gttgagtatg aaaatatttt ttaatgcatt   3957 ttatgacttg ccaattgatt gacaacatgc atcgctgcag acggtaccga gctcgaattc   4017 gtaatcatgg tcatagctgt ttcctgtgtg aaattgttat ccgctcacaa ttccacacaa   4077
```

```
catacgagcc ggaagcataa agtgtaaagc ctggggtgcc taatgagtga gctaactcac    4137
attaattgcg ttgcgctcac tgcccgcttt ccagtcggga aacctgtcgt gccagctgca    4197
ttaatgaatc ggccaacgcg cggggagagg cggtttgcgt attggctaga gcagcttgcc    4257
aacatggtgg agcacgacac tctcgtctac tccaagaata tcaaagatac agtctcagaa    4317
gaccaaaggg ctattgagac ttttcaacaa agggtaatat cgggaaacct cctcggattc    4377
cattgcccag ctatctgtca cttcatcaaa aggacagtag aaaaggaagg tggcacctac    4437
aaatgccatc attgcgataa aggaaaggct atcgttcaag atgcctctgc cgacagtggt    4497
cccaaagatg gacccccacc cacgaggagc atcgtggaaa agaagacgt tccaaccacg    4557
tcttcaaagc aagtggattg atgtgataac atggtggagc acgacactct cgtctactcc    4617
aagaatatca agatacagt ctcagaagac caaagggcta ttgagacttt tcaacaaagg    4677
gtaatatcgg gaacctcct cggattccat tgcccagcta tctgtcactt catcaaaagg    4737
acagtagaaa aggaaggtgg cacctacaaa tgccatcatt gcgataaagg aaaggctatc    4797
gttcaagatg cctctgccga cagtggtccc aaagatggac ccccaccac gaggagcatc    4857
gtggaaaaag aagacgttcc aaccacgtct tcaaagcaag tggattgatg tgatatctcc    4917
actgacgtaa gggatgacgc acaatcccac tatccttcgc aagacccttc ctctatataa    4977
ggaagttcat tcatttggag aggacacgc tgaaatcacc agtctctctc tacaaatcta    5037
tctctctcga ttcgcagatc tgtcgatcga ccatggggat tgaacaagat ggattgcacg    5097
caggttctcc ggccgcttgg gtggagaggc tattcggcta tgactgggca acagacaa     5157
tcggctgctc tgatgccgcc gtgttccggc tgtcagcgca ggggcgcccg gttctttttg    5217
tcaagaccga cctgtccggt gccctgaatg aactccagga cgaggcagcg cggctatcgt    5277
ggctggccac gacgggcgtt ccttgcgcag ctgtgctcga cgttgtcact gaagcgggaa    5337
gggactggct gctattgggc gaagtgccgg ggcaggatct cctgtcatct caccttgctc    5397
ctgccgagaa agtatccatc atggctgatg caatgcggcg gctgcatacg cttgatccgg    5457
ctacctgccc attcgaccac caagcgaaac atcgcatcga gcgagcacgt actcggatgg    5517
aagccggtct tgtcgatcag gatgatctgg acgaagagca tcagggctc gcgccagccg    5577
aactgttcgc caggctcaag gcgcgcatgc ccgacgcga gatctcgtc gtgacacatg    5637
gcgatgcctg cttgccgaat atcatggtgg aaaatggccg cttttctgga ttcatcgact    5697
gtggccggct gggtgtggcg gaccgctatc aggacatagc gttggctacc cgtgatattg    5757
ctgaagagct tggcggcgaa tgggctgacc gcttcctcgt gctttacggt atcgccgctc    5817
ccgattcgca gcgcatcgcc ttctatcgcc ttcttgacga gttcttctga gcgggactct    5877
ggggttcgga tcgatcctct agctagagtc gatcgacatc gagtttctcc ataataatgt    5937
gtgagtagtt cccagataag ggaattaggg ttcttatagg gtttcgctca cgtgttgagc    5997
atataagaaa cccttagtat gtatttgtat ttgtaaaata cttctatcaa taaaatttct    6057
aattcctaaa accaaaatcc agtactaaaa tccagtcac ctaaagtccc tatagatccc    6117
ccgaattaat tcggcgttaa ttcagtacat taaaaacgtc cgcaatgtgt tattaagttg    6177
tctaagcgtc aatttgttta caccacaata tatcctgcca ccagccagcc aacagctccc    6237
cgaccggcag ctcggcacaa aatcaccact cgatacaggc agcccatcag tccgggacgg    6297
cgtcagcggg agagccgttg taaggcggca gactttgctc atgttaccga tgctattcgg    6357
aagaacggca actaagctgc cgggtttgaa acacggatga tctcgcggag ggtagcatgt    6417
tgattgtaac gatgacagag cgttgctgcc tgtgatcaat tcgggcacga acccagtgga    6477
```

| | |
|---|---:|
| cataagcctc gttcggttcg taagctgtaa tgcaagtagc gtaactgccg tcacgcaact | 6537 |
| ggtccagaac cttgaccgaa cgcagcggtg gtaacggcgc agtggcggtt ttcatggctt | 6597 |
| cttgttatga catgtttttt tggggtacag tctatgcctc gggcatccaa gcagcaagcg | 6657 |
| cgttacgccg tgggtcgatg tttgatgtta tggagcagca acgatgttac gcagcagggc | 6717 |
| agtcgcccta aaacaaagtt aaacatcatg ggggaagcgg tgatcgccga agtatcgact | 6777 |
| caactatcag aggtagttgg cgtcatcgag cgccatctcg aaccgacgtt gctggccgta | 6837 |
| catttgtacg gctccgcagt ggatggcggc ctgaagccac acagtgatat tgatttgctg | 6897 |
| gttacggtga ccgtaaggct tgatgaaaca cgcggcgag ctttgatcaa cgacctttg | 6957 |
| gaaacttcgg cttcccctgg agagagcgag attctccgcg ctgtagaagt caccattgtt | 7017 |
| gtgcacgacg acatcattcc gtggcgttat ccagctaagc gcgaactgca atttggagaa | 7077 |
| tggcagcgca atgacattct tgcaggtatc ttcgagccag ccacgatcga cattgatctg | 7137 |
| gctatcttgc tgacaaaagc aagagaacat agcgttgcct tggtaggtcc agcggcggag | 7197 |
| gaactctttg atccggttcc tgaacaggat ctatttgagg cgctaaatga aaccttaacg | 7257 |
| ctatggaact cgccgcccga ctgggctggc gatgagcgaa atgtagtgct tacgttgtcc | 7317 |
| cgcatttggt acagcgcagt aaccggcaaa atcgcgccga aggatgtcgc tgccgactgg | 7377 |
| gcaatggagc gcctgccggc ccagtatcag cccgtcatac ttgaagctag acaggcttat | 7437 |
| cttgacaag aagaagatcg cttggcctcg cgcgcagatc agttggaaga atttgtccac | 7497 |
| tacgtgaaag gcgagatcac caaggtagtc ggcaaataat gtctagctag aaattcgttc | 7557 |
| aagccgacgc cgcttcgccg gcgttaactc aagcgattag atgcactaag cacataattg | 7617 |
| ctcacagcca aactatcagg tcaagtctgc tttattatt tttaagcgtg cataataagc | 7677 |
| cctacacaaa ttgggagata tatcatgcat gaccaaaatc ccttaacgtg agttttcgtt | 7737 |
| ccactgagcg tcagacccg tagaaaagat caaaggatct tcttgagatc cttttttct | 7797 |
| gcgcgtaatc tgctgcttgc aaacaaaaaa accaccgcta ccagcggtgg tttgtttgcc | 7857 |
| ggatcaagag ctaccaactc ttttccgaa ggtaactggc ttcagcagag cgcagatacc | 7917 |
| aaatactgtc cttctagtgt agccgtagtt aggccaccac ttcaagaact ctgtagcacc | 7977 |
| gcctacatac ctcgctctgc taatcctgtt accagtggct gctgccagtg gcgataagtc | 8037 |
| gtgtcttacc gggttggact caagacgata gttaccggat aaggcgcagc ggtcgggctg | 8097 |
| aacggggggt tcgtgcacac agcccagctt ggagcgaacg acctacaccg aactgagata | 8157 |
| cctacagcgt gagctatgag aaagcgccac gcttcccgaa gggagaaagg cggacaggta | 8217 |
| tccggtaagc ggcagggtcg gaacaggaga gcgcacgagg gagcttccag ggggaaacgc | 8277 |
| ctggtatctt tatagtcctg tcgggtttcg ccacctctga cttgagcgtc gatttttgtg | 8337 |
| atgctcgtca ggggggcgga gcctatggaa aaacgccagc aacgcggcct ttttacggtt | 8397 |
| cctggccttt tgctggcctt ttgctcacat gttctttcct gcgttatccc ctgattctgt | 8457 |
| ggataaccgt attaccgcct ttgagtgagc tgataccgct cgccgcagcc gaacgaccga | 8517 |
| gcgcagcgag tcagtgagcg aggaagcgga agagcgcctg atgcggtatt ttctccttac | 8577 |
| gcatctgtgc ggtatttcac accgcatatg gtgcactctc agtacaatct gctctgatgc | 8637 |
| cgcatagtta agccagtata cactccgcta tcgctacgtg actgggtcat ggctgcgccc | 8697 |
| cgacacccgc caaacccgc tgacgcgccc tgacgggctt gtctgctccc ggcatccgct | 8757 |
| tacagacaag ctgtgaccgt ctccgggagc tgcatgtgtc agaggttttc accgtcatca | 8817 |

-continued

```
ccgaaacgcg cgaggcaggg tgccttgatg tgggcgccgg cggtcgagtg gcgacggcgc    8877
ggcttgtccg cgccctggta gattgcctgg ccgtaggcca gccattttttg agcggccagc   8937
ggccgcgata ggccgacgcg aagcggcggg gcgtagggag cgcagcgacc gaagggtagg    8997
cgctttttgc agctcttcgg ctgtgcgctg gccagacagt tatgcacagg ccaggcgggt    9057
tttaagagtt ttaataagtt ttaaagagtt ttaggcggaa aaatcgcctt ttttctctttt   9117
tatatcagtc acttacatgt gtgaccggtt cccaatgtac ggctttgggt tcccaatgta    9177
cgggttccgg ttcccaatgt acggctttgg gttcccaatg tacgtgctat ccacaggaaa    9237
gagacctttt cgaccttttt cccctgctag ggcaatttgc cctagcatct gctccgtaca    9297
ttaggaaccg gcggatgctt cgccctcgat caggttgcgg tagcgcatga ctaggatcgg    9357
gccagcctgc cccgcctcct ccttcaaatc gtactccggc aggtcatttg acccgatcag    9417
cttgcgcacg gtgaaacaga acttcttgaa ctctccggcg ctgccactgc gttcgtagat    9477
cgtcttgaac aaccatctgg cttctgcctt gcctgcggcg cggcgtgcca ggcggtagag    9537
aaaacgccg atgccgggat cgatcaaaaa gtaatcgggg tgaaccgtca gcacgtccgg     9597
gttcttgcct tctgtgatct cgcggtacat ccaatcagct agctcgatct cgatgtactc    9657
cggccgcccg gtttcgctct ttacgatctt gtagcggcta atcaaggctt caccctcgga    9717
taccgtcacc aggcggccgt tcttggcctt cttcgtacgc tgcatggcaa cgtgcgtggt    9777
gtttaaccga atgcaggttt ctaccaggtc gtctttctgc tttccgccat cggctcgccg    9837
gcagaacttg agtacgtccg caacgtgtgg acggaacacg cggccgggct tgtctcccttt   9897
cccttcccgg tatcggttca tggattcggt tagatgggaa accgccatca gtaccaggtc    9957
gtaatcccac acactggcca tgccggccgg ccctgcggaa acctctacgt gcccgtctgg   10017
aagctcgtag cggatcacct cgccagctcg tcggtcacgc ttcgacagac ggaaaacggc   10077
cacgtccatg atgctgcgac tatcgcgggt gcccacgtca tagagcatcg gaacgaaaaa   10137
atctggttgc tcgtcgccct tgggcggctt cctaatcgac ggcgcaccgg ctgccggcgg   10197
ttgccgggat tctttgcgga ttcgatcagc ggccgcttgc cacgattcac cggggcgtgc   10257
ttctgcctcg atgcgttgcc gctgggcggc ctgcgcggcc ttcaacttct ccaccaggtc   10317
atcacccagc gccgcgccga tttgtaccgg gccggatggt ttgcgaccgt cacgccgatt   10377
cctcgggctt gggggttcca gtgccattgc agggccggca gacaacccag ccgcttacgc   10437
ctggccaacc gccgttcct ccacacatgg ggcattccac ggcgtcggtg cctggttgtt    10497
cttgattttc catgccgcct cctttagccg ctaaaattca tctactcatt tattcatttg   10557
ctcatttact ctggtagctg cgcgatgtat tcagatagca gctcggtaat ggtcttgcct   10617
tggcgtaccg cgtacatctt cagcttggtg tgatcctccg ccggcaactg aaagttgacc   10677
cgcttcatgg ctgcgtgtc tgccaggctg gccaacgttg cagccttgct gctgcgtgcg    10737
ctcggacggc cggcacttag cgtgtttgtg cttttgctca ttttctcttt acctcattaa   10797
ctcaaatgag ttttgattta atttcagcgg ccagcgcctg gacctcgcgg gcagcgtcgc   10857
cctcgggttc tgattcaaga acggttgtgc cggcggcggc agtgcctggg tagctcacgc   10917
gctgcgtgat acggactca agaatgggca gctcgtaccc ggccagcgcc tcggcaacct    10977
caccgccgat gcgcgtgcct tgatcgccc gcgacacgac aaaggccgct tgtagccttc    11037
catccgtgac ctcaatgcgc tgcttaacca gctccaccag gtcggcggtg gcccatatgt   11097
cgtaagggct tggctgcacc ggaatcagca cgaagtcggt tgccttgatc gcggacacag   11157
ccaagtccgc cgcctggggc gctccgtcga tcactacgaa gtcgcgccgg ccgatggcct   11217
```

```
tcacgtcgcg gtcaatcgtc gggcggtcga tgccgacaac ggttagcggt tgatcttccc    11277
gcacggccgc ccaatcgcgg gcactgccct ggggatcgga atcgactaac agaacatcgg    11337
ccccggcgag ttgcagggcg cgggctagat gggttgcgat ggtcgtcttg cctgacccgc    11397
ctttctggtt aagtacagcg ataaccttca tgcgttcccc ttgcgtattt gtttatttac    11457
tcatcgcatc atatacgcag cgaccgcatg acgcaagctg ttttactcaa atacacatca    11517 ccttttttaga cggcggcgct cggtttcttc agcggccaag ctggccggcc aggccgccag    11577
```
(Note: line 11517→11577 shows "cctttttaga" in source)

```
cttggcatca gacaaaccgg ccaggatttc atgcagccgc acggttgaga cgtgcgcggg    11637
cggctcgaac acgtacccgg ccgcgatcat ctccgcctcg atctcttcgg taatgaaaaa    11697
cggttcgtcc tggccgtcct ggtgcggttt catgcttgtt cctcttggcg ttcattctcg    11757
gcggccgcca gggcgtcggc ctcggtcaat gcgtcctcac ggaaggcacc gcgccgcctg    11817
gcctcggtgg gcgtcacttc ctcgctgcgc tcaagtgcgc ggtacagggt cgagcgatgc    11877
acgccaagca gtgcagccgc ctctttcacg gtgcggcctt cctggtcgat cagctcgcgg    11937
gcgtgcgcga tctgtgccgg ggtgagggta gggcgggggc caaacttcac gcctcgggcc    11997
ttggcggcct cgcgcccgct ccgggtgcgg tcgatgatta gggaacgctc gaactcggca    12057
atgccggcga acacggtcaa caccatgcgg ccggccggcg tggtggtgtc ggcccacggc    12117
tctgccaggc tacgcaggcc cgcgccggcc tcctggatgc gctcggcaat gtccagtagg    12177
tcgcgggtgc tgcgggccag gcggtctagc ctggtcactg tcacaacgtc gccagggcgt    12237
aggtggtcaa gcatcctggc cagctccggg cggtcgcgcc tggtgccggt gatcttctcg    12297 gaaacagct tggtgcagcc ggccgcgtgc agttcggccc gttggttggt caagtcctgg    12357
```
(line 12357: "gaaaacagct" per source)

```
tcgtcggtgc tgacgcgggc atagcccagc aggccagcgg cggcgctctt gttcatggcg    12417
taatgtctcc ggttctagtc gcaagtattc tactttatgc gactaaaaca cgcgacaaga    12477
aaacgccagg aaaagggcag ggcggcagcc tgtcgcgtaa cttaggactt gtgcgacatg    12537
tcgttttcag aagacggctg cactgaacgt cagaagccga ctgcactata gcagcggagg    12597
ggttggatca aagtact                                                    12614
```

<210> SEQ ID NO 2
<211> LENGTH: 550
<212> TYPE: PRT
<213> ORGANISM: Bacterial Plasmid DNA - Plasmid pZP-ALE

<400> SEQUENCE: 2

```
Met Glu Asp Ala Lys Asn Ile Lys Lys Gly Pro Ala Pro Phe Tyr Pro
  1               5                  10                  15

Leu Glu Asp Gly Thr Ala Gly Glu Gln Leu His Lys Ala Met Lys Arg
                 20                  25                  30

Tyr Ala Leu Val Pro Gly Thr Ile Ala Phe Thr Asp Ala His Ile Glu
         35                  40                  45

Val Asp Ile Thr Tyr Ala Glu Tyr Phe Glu Met Ser Val Arg Leu Ala
     50                  55                  60

Glu Ala Met Lys Arg Tyr Gly Leu Asn Thr Asn His Arg Ile Val Val
 65                  70                  75                  80

Cys Ser Glu Asn Ser Leu Gln Phe Phe Met Pro Val Leu Gly Ala Leu
                 85                  90                  95

Phe Ile Gly Val Ala Val Ala Pro Ala Asn Asp Ile Tyr Asn Glu Arg
                100                 105                 110

Glu Leu Leu Asn Ser Met Gly Ile Ser Gln Pro Thr Val Val Phe Val
```

-continued

```
                115                 120                 125
Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540
```

Gly Gly Lys Ile Ala Val
545                 550

<210> SEQ ID NO 3
<211> LENGTH: 14194
<212> TYPE: DNA
<213> ORGANISM: Bacterial Plasmid DNA-Plasmid pZB-ALN

<400> SEQUENCE: 3

| | | | | |
|---|---|---|---|---|
| gctgcgcatt | ttaacgaaat | ggcctccggc | aaacccggtg | cggttcactt | gttgcgtggg | 60 |
| aaagttcacg | ggactccgcg | cacgagcctt | cttcgtaata | gccatatcga | ccgaattgac | 120 |
| ctgcagggg | gggggggcgc | tgaggtctgc | ctcgtgaaga | aggtgttgct | gactcatacc | 180 |
| aggcctgaat | cgccccatca | tccagccaga | aagtgaggga | gccacggttg | atgagagctt | 240 |
| tgttgtaggt | ggaccagttg | gtgattttga | acttttgctt | tgccacggaa | cggtctgcgt | 300 |
| tgtcgggaag | atgcgtgatc | tgatccttca | actcagcaaa | agttcgattt | attcaacaaa | 360 |
| gccgccgtcc | cgtcaagtca | gcgtaatgct | ctgccagtgt | tacaaccaat | taaccaattc | 420 |
| tgattagaaa | aactcatcga | gcatcaaatg | aaactgcaat | ttattcatat | caggattatc | 480 |
| aataccatat | ttttgaaaaa | gccgtttctg | taatgaagga | gaaaactcac | cgaggcagtt | 540 |
| ccataggatg | gcaagatcct | ggtatcggtc | tgcgattccg | actcgtccaa | catcaataca | 600 |
| acctattaat | ttcccctcgt | caaaaataag | gttatcaagt | gagaaatcac | catgagtgac | 660 |
| gactgaatcc | ggtgagaatg | gcaaaagctt | atgcatttct | ttccagactt | gttcaacagg | 720 |
| ccagccatta | cgctcgtcat | caaaatcact | cgcatcaacc | aaaccgttat | tcattcgtga | 780 |
| ttgcgcctga | gcgagacgaa | atacgcgatc | gctgttaaaa | ggacaattac | aaacaggaat | 840 |
| cgaatgcaac | cggcgcagga | acactgccag | cgcatcaaca | atattttcac | ctgaatcagg | 900 |
| atattcttct | aatacctgga | atgctgtttt | cccggggatc | gcagtggtga | gtaaccatgc | 960 |
| atcatcagga | gtacggataa | aatgcttgat | ggtcggaaga | ggcataaatt | ccgtcagcca | 1020 |
| gtttagtctg | accatctcat | ctgtaacatc | attggcaacg | ctacctttgc | catgtttcag | 1080 |
| aaacaactct | ggcgcatcgg | gcttcccata | caatcgatag | attgtcgcac | ctgattgccc | 1140 |
| gacattatcg | cgagcccatt | tatacccata | taaatcagca | tccatgttgg | aatttaatcg | 1200 |
| cggcctcgag | caagacgttt | cccgttgaat | atggctcata | acacccctg | tattactgtt | 1260 |
| tatgtaagca | gacagttta | ttgttcatga | tgatatattt | ttatcttgtg | caatgtaaca | 1320 |
| tcagagattt | tgagacacaa | cgtggctttc | ccccccccc | ctgcaggtct | tttccaatga | 1380 |
| tgagcacttt | taaagttctg | ctatgtggcg | cggtattatc | ccgtgttgac | gccgggcaag | 1440 |
| agcaactcgg | tcgccgcata | cactattctc | agaatgactt | ggttgagtac | tcaccagtca | 1500 |
| cagaaaagca | tcttacggat | ggcatgacag | taagagaatt | atgcagtgct | gccataacca | 1560 |
| tgagtgataa | cactgcggcc | aacttacttc | tgacaacgat | cggaggaccg | aaggagctaa | 1620 |
| ccgcttttt | gcacaacatg | gggatcatg | taactcgcct | tgatcgttgg | gaaccggagc | 1680 |
| tgaatgaagc | cataccaaac | gacgagcgtg | acaccacgat | gcctgtagca | atggcaacaa | 1740 |
| cgttgcgcaa | actattaact | ggcgaactac | ttactctagc | ttcccggcaa | caattaatag | 1800 |
| actggatgga | ggcggataaa | gttgcaggac | cacttctgcg | ctcggccctt | ccggctggct | 1860 |
| ggtttattgc | tgataaatct | ggagccggtg | agcgtgggtc | tcgcggtatc | attgcagcac | 1920 |
| tggggccaga | tggtaagccc | tcccgtatcg | tagttatcta | cacgacgggg | agtcaggcaa | 1980 |
| ctatggatga | acgaaataga | cagatcgctg | agataggtgc | ctcactgatt | aagcattggt | 2040 |

```
aactgtcaga ccaagtttac tcatatatac tttagattga tttaaaactt cattttttaat   2100 ttaaaaggat ctaggtgaag atcctttttg ataatctcat gaccaaaatc ccttaacgtg   2160
agttttcgtt ccactgagcg tcagacccg  tagaaaagat caaaggatct tcttgagatc    2220 cttttttttct gcgcgtaatc tgctgcttgc aaacaaaaaa accaccgcta ccagcggtgg   2280
tttgtttgcc ggatcaagag ctaccaactc ttttttccgaa ggtaactggc ttcagcagag   2340
cgcagatacc aaatactgtc cttctagtgt agccgtagtt aggccaccac ttcaagaact   2400
ctgtagcacc gcctacatac ctcgctctgc taatcctgtt accagtggct gctgccagtg   2460
gcgataagtc gtgtcttacc gggttggact caagacgata gttaccggat aaggcgcagc   2520
ggtcgggctg aacggggggt tcgtgcacac agcccagctt ggagcgaacg acctacaccg   2580
aactgagata cctacagcgt gagctatgag aaagcgccac gcttcccgaa gggagaaagg   2640
cggacaggta tccggtaagc ggcagggtcg gaacaggaga gcgcacgagg gagcttccag   2700
ggggaaacgc ctggtatctt tatagtcctg tcgggtttcg ccacctctga cttgagcgtc   2760
gatttttgtg atgctcgtca ggggggcgga gcctatggaa aaacgccagc aacgcggcct   2820
ttttacggtt cctggccttt tgctggcctt ttgctcacat gttctttcct gcgttatccc   2880
ctgattctgt ggataaccgt attaccgcct ttgagtgagc tgataccgct cgccgcagcc   2940
gaacgaccga gcgcagcgag tcagtgagcg aggaagcgga agagcgcctg atgcggtatt   3000
ttctccttac gcatctgtgc ggtatttcac accgcatatg gtgcactctc agtacaatct   3060
gctctgatgc cgcatagtta agccagtata cactccgcta tcgctacgtg actgggtcat   3120
ggctgcgccc cgacacccgc caacacccgc tgacgcgccc tgacgggctt gtctgctccc   3180
ggcatccgct tacagacaag ctgtgaccgt ctccgggagc tgcatgtgtc agaggttttc   3240
accgtcatca ccgaaacgcg cgaggcaggg tgccttgatg tgggcgccgg cggtcgagtg   3300
gcgacggcgc ggcttgtccg cgccctggta gattgcctgg ccgtaggcca gccattttg    3360 agcggccagc ggccgcgata ggccgacgcg aagcggcggg gcgtagggag cgcagcgacc   3420
gaagggtagg cgcttttgc agctcttcgg ctgtgcgctg gccagacagt tatgcacagg    3480
ccaggcgggt tttaagagtt ttaataagtt ttaaagagtt ttaggcggaa aaatcgcctt   3540
ttttctcttt tatatcagtc acttacatgt gtgaccggtt cccaatgtac ggctttgggt   3600
tcccaatgta cgggttccgg ttcccaatgt acggctttgg gttcccaatg tacgtgctat   3660
ccacaggaaa gagaccttt  cgaccttttt ccctgctag  gcaatttgc  cctagcatct    3720 gctccgtaca ttaggaaccg gcggatgctt cgccctcgat caggttgcgg tagcgcatga   3780
ctaggatcgg gccagcctgc cccgcctcct ccttcaaatc gtactccggc aggtcatttg   3840
acccgatcag cttgcgcacg gtgaaacaga acttcttgaa ctctccggcg ctgccactgc   3900
gttcgtagat cgtcttgaac aaccatctgg cttctgcctt gctgcggcg cggcgtgcca   3960 ggcggtagag aaaacggccg atgccgggat cgatcaaaaa gtaatcgggg tgaaccgtca   4020
gcacgtccgg gttcttgcct tctgtgatct cgcggtacat ccaatcagct agctcgatct   4080
cgatgtactc cggccgcccg gtttcgctct ttacgatctt gtagcggcta atcaaggctt   4140
caccctcgga taccgtcacc aggcggccgt tcttggcctt cttcgtacgc tgcatggcaa   4200
cgtgcgtggt gtttaaccga atgcaggttt ctaccaggtc gtctttctgc tttccgccat   4260
cggctcgccg gcagaacttg agtacgtccg caacgtgtgg acggaacacg cggcgggct    4320 tgtctccctt cccttcccgg tatcggttca tggattcggt tagatgggaa accgccatca   4380
```

-continued

```
gtaccaggtc gtaatcccac acactggcca tgccggccgg ccctgcggaa acctctacgt    4440
gcccgtctgg aagctcgtag cggatcacct cgccagctcg tcggtcacgc ttcgacagac    4500
ggaaaacggc cacgtccatg atgctgcgac tatcgcgggt gcccacgtca tagagcatcg    4560
gaacgaaaaa atctggttgc tcgtcgccct tgggcggctt cctaatcgac ggcgcaccgg    4620
ctgccggcgg ttgccgggat tctttgcgga ttcgatcagc ggccgcttgc cacgattcac    4680
cggggcgtgc ttctgcctcg atgcgttgcc gctgggcggc ctgcgcggcc ttcaacttct    4740
ccaccaggtc atcacccagc gccgcgccga tttgtaccgg gccggatggt ttgcgaccgc    4800
tcacgccgat tcctcgggct tggggggttcc agtgccattg cagggccggc agacaaccca    4860
gccgcttacg cctggccaac cgcccgttcc tccacacatg gggcattcca cggcgtcggt    4920
gcctggttgt tcttgatttt ccatgccgcc tcctttagcc gctaaaattc atctactcat    4980
ttattcattt gctcatttac tctggtagct gcgcgatgta ttcagatagc agctcggtaa    5040
tggtcttgcc ttggcgtacc gcgtacatct tcagcttggt gtgatcctcc gccggcaact    5100
gaaagttgac ccgcttcatg gctggcgtgt ctgccaggct ggccaacgtt gcagccttgc    5160
tgctgcgtgc gctcggacgg ccggcactta gcgtgttgt gcttttgctc attttctctt    5220
tacctcatta actcaaatga gttttgattt aatttcagcg gccagcgcct ggacctcgcg    5280
ggcagcgtcg ccctcgggtt ctgattcaag aacggttgtg ccggcggcgg cagtgcctgg    5340
gtagctcacg cgctgcgtga tacgggactc aagaatgggc agctcgtacc cggccagcgc    5400
ctcggcaacc tcacgccga tgcgcgtgcc tttgatcgcc cgcgacacga caaggccgc    5460 ttgtagcctt ccatccgtga cctcaatgcg ctgcttaacc agctccacca ggtcggcggt    5520
ggcccatatg tcgtaagggc ttggctgcac cggaatcagc acgaagtcgg ctgccttgat    5580
cgcggacaca gccaagtccg ccgcctgggg cgctccgtcg atcactacga agtcgcgccg    5640 gccgatggc ttcacgtcgc ggtcaatcgt cgggcggtcg atgccgacaa cggttagcgg    5700
ttgatcttcc cgcacggccg cccaatcgcg ggcactgccc tggggatcgg aatcgactaa    5760
cagaacatcg gccccggcga gttgcagggc gcgggctaga tgggttgcga tggtcgtctt    5820
gcctgacccg cctttctggt taagtacagc gataacttca tgcgttccct tgcgtatttg    5880
tttatttact catcgcatca tatacgcagc gaccgcatga cgcaagctgt tttactcaaa    5940
tacacatcac cttttagac ggcggcgctc ggtttcttca gcggccaagc tggccggcca    6000
ggccgccagc ttggcatcag acaaaccggc caggatttca tgcagccgca cggttgagac    6060
gtgcgcgggc ggctcgaaca cgtacccggc cgcgatcatc tccgcctcga tctcttcggt    6120
aatgaaaaac ggttcgtcct ggccgtcctg gtgcggtttc atgcttgttc ctcttggcgt    6180
tcattctcgg cggccgccag ggcgtcggcc tcggtcaatg cgtcctcacg gaaggcaccg    6240
cgccgcctgg cctcggtggg cgtcacttcc tcgctgcgct caagtgcgcg gtacagggtc    6300
gagcgatgca cgccaagcag tgcagccgcc tctttcacgg tgcggccttc ctggtcgatc    6360
agctcgcggg cgtgcgcgat ctgtgccggg gtgagggtag ggcgggggcc aaacttcacg    6420
cctcgggcct tggcggcctc gcgcccgctc cgggtgcggt cgatgattag ggaacgctcg    6480
aactcggcaa tgccggcgaa cacgtcaac accatgcggc cggccggcgt ggtggtgtcg    6540
gcccacggct ctgccaggct acgcaggccc gcgccggcct cctggatgcg ctcggcaatg    6600
tccagtaggt cgcgggtgct gcgggccagg cggtctagcc tggtcactgt cacaacgtcg    6660
ccagggcgta ggtggtcaag catcctggcc agctccgggc ggtcgcgcct ggtgccggtg    6720
atcttctcgg aaaacagctt ggtgcagccg gccgcgtgca gttcggcccg ttggttggtc    6780
```

```
aagtcctggt cgtcggtgct gacgcgggca tagcccagca ggccagcggc ggcgctcttg   6840
ttcatggcgt aatgtctccg gttctagtcg caagtattct actttatgcg actaaaacac   6900
gcgacaagaa aacgccagga aaagggcagg gcggcagcct gtcgcgtaac ttaggacttg   6960
tgcgacatgt cgttttcaga agacggctgc actgaacgtc agaagccgac tgcactatag   7020
cagcggaggg gttggaccac aggacgggtg tggtcgccat gatcgcgtag tcgatagtgg   7080
ctccaagtag cgaagcgagc aggactgggc ggcggccaaa gcggtcggac agtgctccga   7140
gaacgggtgc gcatagaaat tgcatcaacg catatagcgc tagcagcacg ccatagtgac   7200
tggcgatgct gtcggaatgg acgatatccc gcaagaggcc cggcagtacc ggcataacca   7260
agcctatgcc tacagcatcc agggtgacgg tgaacgtcgg ctcgattgta cctgcgttca   7320
aatactttgc gatcgtgttg cgcgcctgcc cggtgcgtcg gctgatctca cggatcgact   7380
gcttctctcg caacgccatc cgacggatga tgtttaaaag tcccatgtgg atcactccgt   7440
tgccccgtcg ctcaccgtgt tgggggaag gtgcacatgg ctcagttctc aatggaaatt   7500
atctgcctaa ccggctcagt tctgcgtaga accaacatg caagctccac cgggtgcaaa   7560
gcggcagcgg cggcaggata tattcaattg taaatggctt catgtccggg aaatctacat   7620
ggatcagcaa tgagtatgat ggtcaatatg gagaaaaaga aagagtaatt accaattttt   7680
tttcaattca aaaatgtaga gtccgcagc gttattataa aatgaaagta cattttgata   7740
aaacgacaaa ttacgatccg tcgtatttat aggcgaaagc aataaacaaa ttattctaat   7800
tcggaaatct ttatttcgac gtgtctacat tcacgtccaa atgggggctt agatgagaaa   7860
cttcacgatc gatgccttga tttcgccatt cccagatacc catttcatct tcagattggt   7920
ctgagattat gcgaaaatat acactcatat acataaatac tgacagtttg agctaccaat   7980
tcagtgtagc ccattacctc acataattca ctcaaatgct aggcagtctg tcaactcggc   8040
gtcaatttgt cggccactat acgatagttg cgcaaatttt caaagtcctg gcctaacatc   8100
acacctctgt cggcggcggg tcccatttgt gataaatcca ccatatcgat acagcaagcg   8160
aaccggaatt gccagctggg gcgccctctg gtaaggttgg gaagccctgc aaagtaaact   8220
ggatggcttt cttgccgcca aggatctgat ggcgcagggg atcaagatca tgagcggaga   8280
attaagggag tcacgttatg accccgccg atgacgcggg acaagccgtt ttacgtttgg   8340
aactgacaga accgcaacga ttgaaggagc cactcagccg cgggtttctg gagtttaatg   8400
agctaagcac atacgtcaga aaccattatt gcgcgttcaa aagtcgccta aggtcactat   8460
cagctagcaa atatttcttg tcaaaaatgc tccactgacg ttccataaat tccctcggt   8520 atccaattag agtctcatat tcactctcaa ccagatcat gagcggagaa ttaagggagt   8580
cacgttatga ccccgccga tgacgcggga caagccgttt tacgtttgga actgacagaa   8640
ccgcaacgat tgaaggagcc actcagccgc gggtttctgg agtttaatga gctaagcaca   8700
tacgtcagaa accattattg cgcgttcaaa agtcgcctaa ggtcactatc agctagcaaa   8760
tatttcttgt caaaaatgct ccactgacgt tccataaatt ccctcggta tccaattaga   8820 gtctcatatt cactctcaat ccagatccgg cccatgatca tgtggattga acaagatgga   8880
ttgcacgcag gttctccggc cgcttgggtg gagaggctat tcggctatga ctgggcacaa   8940
cagacaatcg gctgctctga tgccgccgtg ttccggctgt cagcgcaggg gcgcccggtt   9000
ctttttgtca agaccgacct gtccggtgcc ctgaatgaac tgcaggacga ggcagcgcgg   9060
ctatcgtggc tggccacgac gggcgttcct tgcgcagctg tgctcgacgt tgtcactgaa   9120
```

```
gcgggaaggg actggctgct attgggcgaa gtgccgggc aggatctcct gtcatctcac      9180
cttgctcctg ccgagaaagt atccatcatg gctgatgcaa tgcggcggct gcatacgctt      9240
gatccggcta cctgcccatt cgaccaccaa gcgaaacatc gcatcgagcg agcacgtact      9300
cggatggaag ccggtcttgt cgatcaggat gatctggacg aagagcatca ggggctcgcg      9360
ccagccgaac tgttcgccag gctcaaggcg cgcatgcccg acggcgagga tctcgtcgtg      9420
acccatggcg atgcctgctt gccgaatatc atggtggaaa atggccgctt ttctggattc      9480
atcgactgtg gccggctggg tgtggcggac cgctatcagg acatagcgtt ggctacccgt      9540
gatattgctg aagagcttgg cggcgaatgg gctgaccgct tcctcgtgct ttacggtatc      9600
gccgctcccg attcgcagcg catcgccttc tatcgccttc ttgacgagtt cttctgagcg      9660
ggactctggg gttcgaaatg accgaccaag cgacgcccaa cctgccatca cgagatttcg      9720
attccaccgc cgccttctat gaaaggttgg gcttcggaat cgttttccgg gacgccggct      9780
ggatgatcct ccagcgcggg gatctcatgc tggagttctt cgcccacccc ctgctttaat      9840
gagatatgcg agacgcctat gatcgcatga tatttgcttt caattctgtt gtgcacgttg      9900
taaaaaacct gagcatgtgt agctcagatc cttaccgccg gtttcggttc attctaatga      9960
atatatcacc cgttactatc gtattttat gaataatatt ctccgttcaa tttactgatt     10020
gtaccctact acttatatgt acaatattaa atgaaaaca atatattgtg ctgaataggt     10080
ttatagcgac atctatgata gagcgccaca ataacaaaca attgcgtttt attattacaa     10140
atccaatttt aaaaaagcg gcagaaccgg tcaaacctaa aagactgatt acataaatct     10200
tattcaaatt tcaaaggcc ccaggggcta gtatctacga cacaccgagc ggcgaactaa     10260
taacgttcac tgaagggaac tccggttccc cgccggcgcg catgggtgag attccttgaa     10320
gttgagtatt ggccgtccgc tctaccgaaa gttacgggca ccattcaacc cggtccagca     10380
cggcggccgg gtaaccgact tgctgccccg agaattatgc agcatttttt tggtgtatgt     10440
gggcccccaaa tgaagtgcag gtcaaaccctt gacagtgacg acaaatcgtt gggcgggtcc     10500
agggcgaatt ttgcgacaac atgtcgaggc tcagcagggg ctcgatcccc tcgcgagttg     10560
gttcagctgc tgcctgaggc tggacgacct cgcggagttc taccggcagt gcaaatccgt     10620
cggcatccag gaaaccagca gcggctatcc gcgcatccat gccccgaac tgcaggagtg     10680
gggaggcacg atggccgctt tggtcgatcg acggatcgat ccattcgcca ttcaggctgc     10740
gcaactgttg ggaagggcga tcggtgcggg cctcttcgct attacgccag ctggcgaaag     10800
gggatgtgc tgcaaggcga ttaagttggg taacgccagg gttttcccag tcacgacgtt     10860
gtaaaacgac ggccagtgaa ttcgagctcg gtacccgggg atcctgtcta gaccatggtt     10920
gtcgactcta gaggatctgt ccattaaacc ccactaaaat gaagtaggct tgaatccatc     10980
atatataaat gttaaattaa tagggctggg aaaaaaacg aaaaccgaaa aaccgaaccg     11040
taccaaacca aaacaaatgg tttggtttgg ttatggtttt gtataaaaac ccatttggtt     11100
gtaattttta tttaagtttt ggttttaggtt tggtttgatt aaaaaccgta aaaccgaacg     11160
tttcttttgt ttttgattta aattaaaaat aattgtatat atatatatat ataatgttca     11220
tttgataaca tgtatctat caaactatcg aaaacaaaa ccctaactgt aacctaaact     11280
aaaattctat ataaattaca tgctgtcatt taggatttga gtttacaaat tagattttga     11340
ttttattttat gcatcacact tataattttt tttggtaaaa acatgaaaaa accgaaacca     11400
aaccggaacc gatccgaacc aaaatacata tggtttttaa atggttttaa ttttttaaaa     11460
ccaaaaactg taaaaccgtt aaaaccgaac cgtaaccaaa ccgaattta tatggttttt     11520
```

```
atatggtttt acttttctta aaatcgaaaa accgtaaaac ctaaaaccga atcaaaacca   11580
aaccgaaaaa ctgaacgtcc aacccttaaa tataatgaaa atcgaatgaa tttgtttgaa   11640
agaatcgaac aaaattgaca ataaaatcta attaggacta ttttcgtcta attttgactt   11700
agttgaaaca gaatattagc aaaaatacta aaacaccaca acgcgtaata atacccacac   11760
acgatatcat taaatttgac caataagaat ctagctcttg gcgaccacgc aagtatcttc   11820
catcttgctc tccaagaaaa atctacaccg gctttaaatt tacataaaca ccctcagtca   11880
aagaaaagtc gtaaacatag tctctctcat gaccacaagg gtaacacagt catcctaaat   11940
ataaaccaca caagaaaact gttatacttt atacacgtgt catagtctca ttacatctac   12000
gtgaagagtt tcgatcatca accgttcgtt ttcttactat ataaaccttg ctcgagacct   12060
gcgtgtgaag cgtataaaga cgacaaagta aaccaaaaaa aaaaagagtt ctcctacaat   12120
tttcctaaat tcttggattt gagatttcac ttttttccgat ttgaaagctt tccatggaag   12180
acgccaaaaa cataaagaaa ggcccggcgc cattctatcc gctggaagat ggaaccgctg   12240
gagagcaact gcataaggct atgaagagat acgccctggt tcctggaaca attgctttta   12300
cagatgcaca tatcgaggtg gacatcactt acgctgagta cttcgaaatg tccgttcggt   12360
tggcagaagc tatgaaacga tatgggctga atacaaatca cagaatcgtc gtatgcagtg   12420
aaaactctct tcaattcttt atgccggtgt tgggcgcgtt atttatcgga gttgcagttg   12480
cgcccgcgaa cgacatttat aatgaacgtg aattgctcaa cagtatgggc atttcgcagc   12540
ctaccgtggt gttcgtttcc aaaaagdggt tgcaaaaaat tttgaacgtg caaaaaaagc   12600
tcccaatcat ccaaaaaatt attatcatgg attctaaaac ggattaccag ggatttcagt   12660
cgatgtacac gttcgtcaca tctcatctac ctcccggttt taatgaatac gattttgtgc   12720
cagagtcctt cgatagggac aagacaattg cactgatcat gaactcctct ggatctactg   12780
gtctgcctaa aggtgtcgct ctgcctcata gaactgcctg cgtgagattc tcgcatgcca   12840
gagatcctat ttttggcaat caaatcattc cggatactgc gattttaagt gttgttccat   12900
tccatcacgg ttttggaatg tttactacac tcggatattt gatatgtgga tttcgagtcg   12960
tcttaatgta tagatttgaa gaagagctgt ttctgaggag ccttcaggat tacaagattc   13020
aaagtgcgct gctggtgcca acccctattct ccttcttcgc caaaagcact ctgattgaca   13080
aatacgattt atctaattta cacgaaattg cttctggtgg cgctcccctc tctaaggaag   13140
tcggggaagc ggttgccaag aggttccatc tgccaggtat caggcaagga tatggctca   13200 ctgagactac atcagctatt ctgattacac ccgaggggga tgataaaccg ggcgcggtcg   13260
gtaaagttgt tccattttt gaagcgaagg ttgtggatct ggataccggg aaaacgctgg   13320
gcgttaatca aagaggcgaa ctgtgtgtga gaggtcctat gattatgtcc ggttatgtaa   13380
acaatccgga agcgaccaac gccttgattg acaaggatga tggctacat tctggagaca   13440 tagcttactg ggacgaagac gaacacttct tcatcgttga ccgcctgaag tctctgatta   13500
agtacaaagg ctatcaggtg gctcccgctg aattggaatc catcttgctc caacacccca   13560
acatcttcga cgcaggtgtc gcaggtcttc ccgacgatga cgccggtgaa cttcccgccg   13620
ccgttgttgt tttggagcac ggaaagacga tgacggaaaa agagatcgtg gattacgtcg   13680
ccagtcaagt aacaaccgcg aaaaagttgc gcggaggagt tgtgtttgtg gacgaagtac   13740
cgaaaggtct taccggaaaa ctcgacgcaa gaaaaatcag agagatcctc ataaaggcca   13800
agaagggcgg aaagatcgcc gtgtaattct agagaattcc taaagaagga gtgcgtcgaa   13860
```

-continued

| | |
|---|---|
| gcagatcgtt caaacatttg gcaataaagt ttcttaagat tgaatcctgt tgccggtctt | 13920 |
| gcgatgatta tcatataatt tctgttgaat tacgttaagc atgtaataat taacatgtaa | 13980 |
| tgcatgacgt tatttatgag atgggttttt atgattagag tcccgcaatt atacatttaa | 14040 |
| tacgcgatag aaaacaaaat atagcgcgca aactaggata aattatcgcg cgcggtgtca | 14100 |
| tctatgttac tagatcgatg tcgacggcag gatatatacc gttgtaattt gagctcgtgt | 14160 |
| gaataagtcg ctgtgtatgt ttgtttgatt catg | 14194 |

<210> SEQ ID NO 4
<211> LENGTH: 1308
<212> TYPE: DNA
<213> ORGANISM: Plant DNA

<400> SEQUENCE: 4

| | |
|---|---|
| aagcttgcat gcctgcaggt cgactctaga ggatccccca gcttgcatgc ctgcaggtcg | 60 |
| actctagagg atcgtccat taaaccccac taaaatgaag taggcttgaa tccatcatat | 120 |
| ataaatgtta aattaatagg gctgggaaaa aaacgaaaaa ccgaaaaacc gaaccgtacc | 180 |
| aaaccaaaac aaatggtttg gtttggttat ggttttgtat aaaaacccat ttggttgtaa | 240 |
| tttttattta agttttggtt taggtttggt ttgattaaaa accgtaaaac cgaacgtttc | 300 |
| ttttgttttt gatttaaatt aaaaataatt gtatatatat atatatataa tgttcatttg | 360 |
| ataacatgat atctatcaaa ctatcgaaaa acaaaaccct aactgtaacc taaactaaaa | 420 |
| ttctatataa attacatgct gtcatttagg atttgagttt acaaattaga ttttgatttt | 480 |
| atttatgcat cacacttata attttttttg gtaaaaacat gaaaaaaccg gaaccaaacc | 540 |
| ggaaccgatc cgaaccaaaa tacatatggt ttttaaatgg ttttaatttt ttaaaaccaa | 600 |
| aaactgtaaa accgttaaaa ccgaaccgta accaaaccga attttatatg gtttttatat | 660 |
| ggttttactt ttcttaaaat cgaaaaaccg taaaacctaa aaccgaatca aaaccaaacc | 720 |
| gaaaaactga acgtccaacc cttaaatata atgaaaatcg aatgaatttg tttgaaagaa | 780 |
| tcgaacaaaa ttgacaataa aatctaatta ggactatttt cgtctaattt tgacttagtt | 840 |
| gaaacagaat attagcaaaa atactaaaac accacaacgc gtaataatac ccacacacga | 900 |
| tatcattaaa tttgaccaat aagaatctag ctcttggcga ccacgcaagt atcttccatc | 960 |
| ttgctctcca agaaaaatct acaccggctt taaatttaca taaacaccct cagtcaaaga | 1020 |
| aaagtcgtaa acatagtctc tctcatgacc acaagggtaa cacagtcatc ctaaatataa | 1080 |
| accacacaag aaaactgtta tactttatac acgtgtcata gtctcattac atctacgtga | 1140 |
| agagtttcga tcatcaaccg ttcgttttct tactatataa accttgctcg agacctgcgt | 1200 |
| gtgaagcgta taaagacgac aaagtaaacc aaaaaaaaaa agagttctcc tacaattttc | 1260 |
| ctaaattctt ggatttgaga tttcactttt tccgatttga aaccatgg | 1308 |

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Bgl 11
    Primer

<400> SEQUENCE: 5

| | |
|---|---|
| ccatagatct gtccattaaa ccccac | 26 |

<210> SEQ ID NO 6

-continued

```
<211> LENGTH: 24
<212> TYPE: DNA
<213> ORGANISM: Artificial Sequence
<220> FEATURE:
<223> OTHER INFORMATION: Description of Artificial Sequence: NCO1 Primer

<400> SEQUENCE: 6
gttatcacca tggtttcaaa tcgg                                              24
```

METHOD FOR IDENTIFYING COMPONENTS INVOLVED IN SIGNAL TRANSDUCTION PATHWAYS IN HIGHER PLANTS

CROSS-REFERENCE TO RELATED APPLICATIONS

This application claims priority from U.S. provisional application Serial No. 60/136,145 entitled "A Reporter System Comprising the *Arabidopsis thaliana* AOX1a Promoter and the Firefly Luciferase Gene to Elucidate the Signal Transduction Pathway Between Mitochondrial Status and Nuclear Gene Expression in Higher Plants", now abandoned, filed by the University of Nebraska on May 20, 1999, which is hereby incorporated by reference in its entirety.

FIELD OF THE INVENTION

The current invention is directed toward a method for identifying components involved in signal transduction pathways in higher plants. In particular, the present invention relates to a method to elucidate key nucleic acid sequences of components involved in the signal transduction pathway that communicates mitochondrial function and metabolic status to nuclear gene expression. The present invention also relates to a method for identifying key nucleic acid sequences of components in the signal transduction pathway between branched chain amino acid biosynthetic pathways and nuclear gene expression. Additionally, the present invention also relates to a polynucleotide that encodes a portion of an AOX promoter, AOX1a, operably linked to a luciferase reporter gene. The present invention also relates to a recombinant vector, transformed cells, and transformed organisms containing this polynucleotide.

BACKGROUND OF THE INVENTION

Mitochondria play a crucial role in the overall physiology of an organism and are a primary site of energy production in all eukaryotic cells. The products of carbohydrate, lipid, and protein catabolism enter the mitochondria and are oxidized by the tricarboxylic acid cycle (TCA) leading to the production of reducing equivalents (NADH and succinate), ATP, and $CO_2$ (Mackenzie et al., (1999) Plant Cell 11:571–586). Energy production occurs as the reducing equivalents NADH and succinate are oxidized and the electrons are fed into a series of enzyme complexes called the mitochondrial electron transport (or respiratory) chain (mtETC). In most eukaryotes, the electrons are passed through the mtETC via the cytochrome respiratory pathway (FIG. 1). In this pathway, electrons move through the mtETC from complex I (NADH dehydrogenase), or complex II (succinate dehydrogenase) or the internal rotenone-insensitive, external and outer membrane NAD(P)H dehydrogenases to the ubiquinone pool. Electrons are then transferred to complex III, then to diffusible cytochrome c and finally to complex IV, which utilizes the electrons to reduce oxygen to water. At several points in the pathway, protons are pumped from the matrix to the intermembrane space, establishing a proton gradient across the inner membrane. The proton gradient is then utilized by complex V (ATPase) to drive the synthesis of ATP. Hence, the cytochrome pathway couples oxidation to the synthesis of ATP. ATP is primary source of chemical energy in the cell.

In higher plants, some fungi, unicellular green algae, and trypanosomes, however, an alternative mtETC pathway exists (referred to as the alternative respiratory pathway) (FIG. 1). In the alternative respiratory pathway, electrons can move from the ubiquione pool to alternative oxidase (AOX), which also reduces oxygen to water (Mackenzie et al., (1999) Plant Cell 11:571–586). AOX does not pump protons and therefore, this pathway results in either a much lower or no establishment of a proton gradient. The end result of the alternative oxidase pathway is an uncoupling of electron transport from ATP synthesis wherein the energy from electron transport is dissipated as heat instead of being harnessed for the production of ATP. The function of the alternative pathway has yet to be fully elucidated, however, proposed functions include 1) an overflow for electrons when the cytochrome pathway is saturated; 2) a means of allowing continued carbon skeleton turnover and conversion when cellular energy is high; and 3) an elimination system for reactive oxygen species. In addition, AOX activity has been shown to be influenced by environmental, developmental, chemical and tissue specific signals (Aubert et al., (1997) Plant J. 11:649–657; and Mackenzie et al., (1999) Plant Cell 11:571–586).

In order to preserve mitochondrial integrity, plants must perceive and respond to numerous developmental changes and environmental stresses. It is of particular importance for plants, that must survive in place, to be able to adapt to harsh environmental conditions. At the molecular level, one mechanism plants and other organisms have in their repertoire to cope with such conditions is the alteration of protein expression. For example, plants alter the expression of proteins in the mtETC as a means to ensure that electron flow is correctly partitioned between the cytochrome and alternative oxidase pathways to meet the energy demands of the cell at any given time. Additionally, numerous environmental stresses and developmental signals can alter the protein profile of mitochondria (Sachs et al., (1986) Ann. Rev. of Plant Physiol. 37:363–376). For example, in response to heat-stress a new class of proteins is induced (the so called "heat shock" proteins) to help ameliorate the impact of heat-stress on the plant (Waters et al., (1996) J. Exp. Bot. 47:325–338). Plants also alter protein expression in response to a number of other environmental stresses including but not limited to: phosphate deficiency, cold stress, aging, salt stress and elevated $CO_2$ levels.

The means by which plant mitochondria alter protein expression is complicated and remains largely enigmatic. The mitochondria has a genome of its own, however, only 10% of the genes needed by the mitochondria are encoded by its genome (Schuster et al., (1994) Ann. Rev. Plant Mol. Biol. 45:61–78). Thus, most mitochondrial proteins are the products of nuclear genes that are imported into the mitochondria from the cytosol following their synthesis. The means by which mitochondrial status is communicated to the nucleus is through a signal transduction pathway (de Winde et al., (1993) *Saccharomyces cerevisiae.* Prog. Nucleic Acid Res. Mol. Biol. 46:51–91; Poyton et al., (1 996) Annu. Rev. Biochem. 65:563–607; and Zitomer et al., (1992) *Saccharomyces cerevisiae.* Microbiol. Rev. 56:1–11). Signal transduction pathways are one mechanism that the cell uses to respond to the surrounding environment (Lewin B. (1997) Genes VI, Oxford University Press, 1053–1082). Through a series of reactions involving numerous protein components and secondary messengers, signal transduction pathways communicate environmental status to the nucleus so that gene expression is tailored to meet the protein demands resulting from the environmental or developmental changes.

Organisms must also regulate the expression of genes encoding proteins involved in branched chain amino acid biosynthesis and likely accomplish this through signal transduction pathways. Acetolactate synthase catalyzes the first committed step in the pathway and its inhibition leads to metabolic perturbation, which results in a lack of branched chain amino acids (Aubert et al., (1997) Plant J. 11:649–657; and Bryan J. K. (1980) The Biochemistry of Plants: A Comprehensive Treatise, Academic Press 5:403–452). Inhibition of branched chain amino acid biosynthesis has been shown to result in an accumulation of AOX protein and transcript (Aubert et al., (1997) Plant J. 11:649–657). Specifically, the herbicides sulfmometuron methyl, chlorsulfuron and sceptor have all been shown to inhibit branched chain amino acid biosynthesis and result in an increase in AOX transcription (Aubert et al., (1997) Plant J. 11:649–657). Hence, characterizing the signal transduction pathway between branched chain amino acid biosynthetic pathways and nuclear gene expression is of particular interest in plants because of the impact that herbicides can have on overall plant metabolism. For example, understanding the mechanism by which specific metabolic enzyme expression is altered in response to herbicide application may provide a means to control the overall response of plants to herbicides.

Research methods to efficiently and comprehensively determine the mechanism of signal transduction pathways have not been fully developed. Characterizing key components involved in signal transduction pathways is a formidable challenge due to the number of protein components that participate in transmitting the signal, the complex biochemical mechanism by which the signal is transmitted, and the impact of signal on both gene expression and protein translation. And, as such, the components involved in the signal transduction pathway that communicates mitochondrial status to nuclear genes have not been determined. Additionally, the components involved in the signal transduction pathways between branched chain amino acid biosynthetic pathways and nuclear gene expression have also not been characterized.

A number of hybridization-based approaches maybe employed in order to identify components of such signal transduction pathways. The Northern Blot is one such procedure that has been utilized to detect a RNA sequence encoding proteins whose expression is altered. However, this method is extremely laborious and inefficient when the goal of the study is to identify unknown components in a signal transduction pathway leading to altered gene expression. Literally, employing this technique may necessitate probing for every mRNA sequence in each mutant plant to identify the gene with the mutation.

Gene tagging based approaches, such as T-DNA tagging, are other methods that have been employed to determine components of a signal transduction pathway (Walbot V., (1992) Ann. Rev. Plant Phys. Mol. Biol. 43:49–82). The idea behind T-DNA gene tagging is that a mobile or introduced piece of DNA can sometimes insert into a gene, and thereby modify gene expression. These "mutated" genes are now "tagged" with foreign DNA. By using a probe for the introduced DNA tag, one can identify genomic clones that contain the DNA tag, and therefore the gene that is mutated. However, like hybridization based techniques, gene tagging also presents significant shortcomings. The primary shortcoming of this approach for screening mutants in a signal transduction pathway is developing a reliable screening technique. The only phenotype may be altered gene expression and the only way to screen in this case, would again, be to perform Northern Blots for each T-DNA mutant.

In order to overcome these shortcomings, recent approaches to identify components in signal transduction pathways have focused on the use of reporter systems to determine mutants of interest in conjunction with genetic techniques to identify the gene with the mutation. A reporter gene is a coding region, which when expressed displays an easily assayed and novel phenotype or biochemistry in the organism, thus reporting on the activity of a promoter to which it is operably linked. A reporter based approach has been used to identify mutants in the signal transduction pathways in *Arabidopsis thaliana* for circadian rhythm, osmotic and cold stress (Millar et al., (1995) Science 267:1161–1163and 1163–1166; and Ishitani et al., (1998) Plant Cell 10:1151–1161). However, Millar and Ishitani do not teach or suggest a reporter system to identify components of either the signal transduction pathway that communicates mitochondrial status to nuclear gene expression or the signal transduction pathway between branched chain amino acid biosynthetic pathways and nuclear gene expression.

SUMMARY OF THE INVENTION

Among the objects of the present invention is the provision of a method to efficiently and comprehensively identify components involved in these signal transduction pathways that communicate mitochondrial status to nuclear gene expression and between branched chain amino acid pathways and gene expression. The elucidation of key proteins in these signal transduction pathways will allow plants to be genetically engineered for increased productivity, herbicide resistance, pest resistance or increased stress tolerance. The current invention meets this need.

The present invention provides a method to identify components of the signal transduction pathways either between mitochondrial status and nuclear gene expression or between branched chain amino acid biosynthetic pathways and nuclear gene expression. This method, unlike current approaches, provides a means to efficiently and comprehensively identify nucleic acid sequences encoding protein components of the pathways by utilizing a novel reporter system.

Accordingly, among the aspects of the present invention is to provide a method for identifying the nucleic acid sequence of components of the signal transduction pathways between mitochondrial function and metabolic status and nuclear gene expression in higher plants comprising:
  (a) transformation of a plant with a vector that encodes a reporter gene operably linked to an AOX promoter;
  (b) identification of a transgenic plant that increases the expression of the reporter gene relative to the basal level of endogenous expression of such gene when subjected to a stimuli;
  (c) mutagenesis of the transgenic plant identified in step b;
  (d) selection of a mutant transgenic plant from step c, wherein such plant exhibits altered expression of the reporter gene; and
  (e) determining the identity of a gene from the mutant plant from step d that encodes a protein that participates in such signal transduction pathway.

Another aspect of the invention is a method to identify the nucleic acid sequence of components of the signal transduction pathways between branched chain amino acid biosynthetic pathways and nuclear gene expression in higher plants comprising:
  (a) transformation of a plant with a vector that encodes a reporter gene operably linked to an AOX promoter;

(b) identification of a transgenic plant that increases the expression of the reporter gene relative to the basal level of endogenous expression of such gene when subjected to a stimuli;

(c) mutagenesis of the transgenic plant identified in step b;

(d) selection of a mutant transgenic plant from step c, wherein such plant exhibits altered expression of the reporter gene; and (e) determining the identity of a gene from the mutant plant from step d that encodes a protein that participates in such signal transduction pathway.

Yet another aspect of the invention is a recombinant vector comprising a member selected from the group consisting of:

(a) a polynucleotide which has the nucleic acid sequence comprising bases 361 through 3317 of SEQ ID NO:1. or the complement thereof;

(b) a polynucleotide that has at least 90% sequence identity with the polynucleotide of (a);

(c) a polynucleotide that hybridizes to the polynucleotide of (a) under conditions of 5×SSC, 50% formamide and 42° C., and which encodes a protein having the same biological function;

(d) a polynucleotide encoding the same amino acid sequence as (a), but which exhibits regular degeneracy in accordance with the degeneracy of the genetic code;

(e) a polynucleotide encoding the same amino acid sequence as (b), but which exhibits regular degeneracy in accordance with the degeneracy of the genetic code; and (f) a polynucleotide encoding the same amino acid sequence as (c), but which exhibits regular degeneracy in accordance with the degeneracy of the genetic code.

Another aspect of the invention is a recombinant polynucleotide comprising a member selected from the group consisting of:

(a) a polynucleotide comprising bases 361 through 3317 of SEQ ID NO: 1 or the complement thereof;

(b) a polynucleotide that has at least 90% sequence identity with the polynucleotide of (a);

(c) a polynucleotide that hybridizes to the polynucleotide of (a) under conditions of 5×SSC, 50% from amide and 42° C., and which encodes a protein having the same biological function;

(d) a polynucleotide encoding the same amino acid sequence as (a), but which exhibits regular degeneracy in accordance with the degeneracy of the genetic code;

(e) a polynucleotide encoding the same amino acid sequence as (b), but which exhibits regular degeneracy in accordance with the degeneracy of the genetic code; and (f) a polynucleotide encoding the same amino acid sequence as (c), but which exhibits regular degeneracy in accordance with the degeneracy of the genetic code.

Yet another aspect of the invention is a recombinant host cell transformed with a vector described above.

Another aspect provides an organism transformed with the vector described above.

A further aspect provides a recombinant host cell transformed with a recombinant polynucleotide described above.

In yet another aspect of the invention provides a recombinant organism transformed with a recombinant polynucleotide described above.

Other features of the present invention will be in part apparent to those skilled in the art and in part pointed out in the detailed description provided below.

BRIEF DESCRIPTION OF THE DRAWINGS

These and other features, aspects, and advantages of the present invention will become better understood with regard to the following description, appended claims and accompanying figures where:

FIG. 6A shows artificially colored image from CCD camera of luminescence from vector pZB-ALN8 plants due to luciferase expression after 8 h of AA treatment;

FIG. 6B depicts CCD camera image of the same plate set forth in FIG. 6A made in white light as a reference; and FIG. 6C depicts dose response curves showing quantitation of luciferase luminescence from pZB-ALN 8 plants at the indicated duration of continuous AA treatment as indicated.

ABBREVIATIONS AND DEFINITIONS

Figure 1:
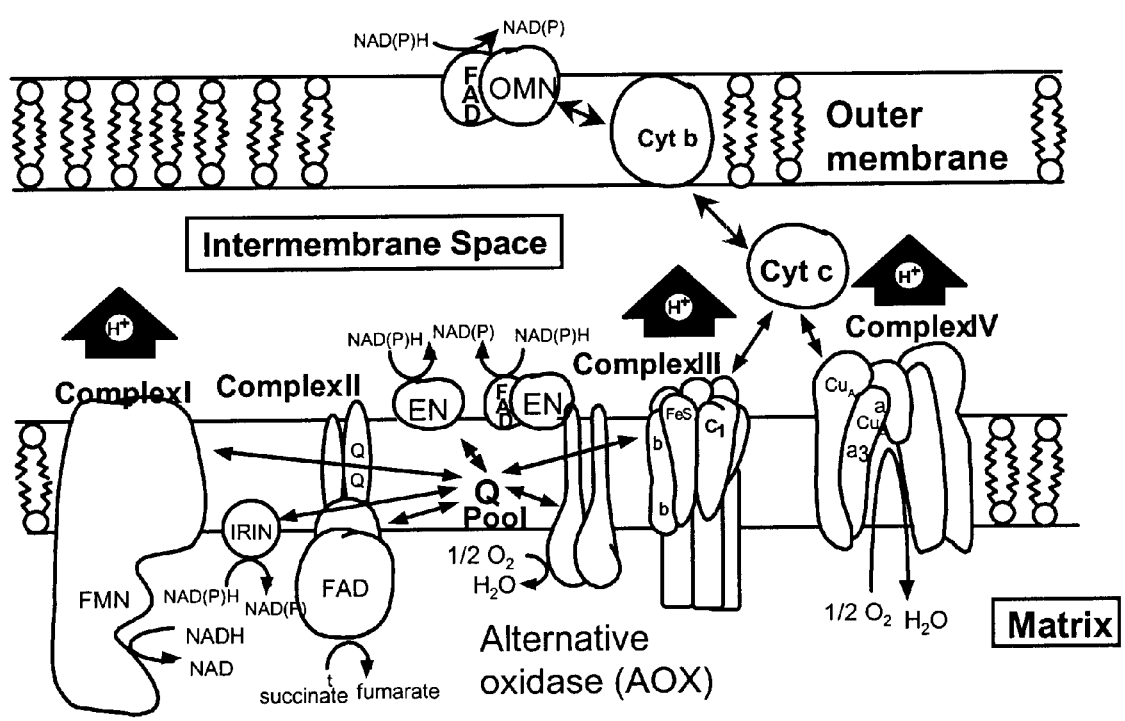
FIG. 1 depicts the higher plant mtETC, with the cytochrome pathway and the alternative pathway diverging after the ubiquinone pool.

To facilitate understanding of the invention, a number of terms and abbreviations as used herein are defined below:

"Altered expression" means increased or decreased transcription directed by a promoter following a stimulus or change in development relative to the expression level of control organisms containing the same gene or transgene and subjected to the same stimulus.

"Mutagen" means any physical or chemical agent that is capable of increasing the frequency of mutation above the spontaneous, background level.

"Mutagenize" means to treat organisms or cells with a mutagen.

"Mutant" means any organism that has arisen by or has undergone mutation or one that carries a mutant gene that is expressed in the phenotype of that organism.

"Operably linked" means a unit of coordinated and regulated gene activity by means of which the control and synthesis of a protein is determined. It then consists of a DNA region encoding a protein together with one or more regions that regulate transcription, such as a promoter.

"Transgene" means a gene inserted into the genome of the germ and somatic cells in a manner that ensures its function, replication and transmission as a normal gene.

"Transgenic" means an organism harboring in its genome of its germ and somatic cells a transgene that has been introduced using recombinant technology.

"Complementary" or "complementarity" refer to the pairing of bases, purines and pyrimidines, that associate through hydrogen bonding in double stranded nucleic acid. The following base pairs are complementary: guanine and cytosine; adenine and thymine; and adenine and uracil. The terms as used herein the terms include complete and partial complementarity.

"Hybridization" refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Thus the term contemplates partial as well as complete hybridization. Such techniques and conditions are well known to practitioners in this field.

"Recombinant nucleic acid" is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequences derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design.

"Polynucleotide" and "oligonucleotide" are used interchangeably and mean a polymer of at least 2 nucleotides joined together by phosphodiester bonds and may consist of either ribonucleotides or deoxyribonucleotides.

"Sequence" or "nucleic acid sequence" means the linear order in which monomers occur in a polymer, for example, the order of amino acids in a polypeptide or the order of nucleotides in a polynucleotide.

"Stimuli" means an increase or decrease in any chemical compound, endogenous or exogenously applied, in a cell of an organism and/or any change in environmental conditions of the organism and includes any increase or decrease in any chemical compounds resulting from the application of any treatment.

"Metabolic perturbation" means any increase or decrease in a substrate or product of any metabolic pathway that occurs in a cell of an organism at any developmental stage of such organism.

"Inhibition of mtETC" means the cessation or decrease in the flow of electrons through the cytochrome respiratory pathway due to any cause and any changes in the concentration of any chemical compound in a cell that results from the cessation or decrease in the flow of electrons through the cytochrome respiratory pathway.

"Inhibition of branched chain amino acid biosynthesis" means the cessation or decrease in any of the enzymatic reactions associated with the synthesis of branched chain amino acids due to any cause and any changes in the concentration of any chemical compound in a cell that results from the cessation or decrease in any of the enzymatic reactions associated with the synthesis of branched chain amino acids.

| | |
|---|---|
| AA = | Antimycin A |
| AOX = | Alternative Oxidase including any homologs thereof |
| ATP = | Adenosine 5'-triphosphate |
| CCD = | Charge-Coupled Device |
| HSP = | Heat Shock Protein |
| NADH = | Nicotinamide-adenine Dinucleotide (reduced form) |
| NAD(P)H = | Nicotinamide-adenine Dinucleotide Phosphate (reduced form) |
| mtETC = | Mitochondrial Electron Transport Chain |
| SA | =Salicylic Acid |
| SMM = | Sulfometuron Methyl |
| TCA = | Tricarboxylic Acid Cycle |

DESCRIPTION OF THE PREFERRED EMBODIMENT

All publications, patents, patent applications and other references cited in this application are herein incorporated by reference in their entirety as if each individual publication, patent, patent application or other reference were specifically and individually indicated to be incorporated.

Applicants have discovered a novel method for elucidating nucleic acid sequences of components involved in the signal transduction pathway that communicates mitochondrial status to nuclear gene expression utilizing a unique reporter system. Applicants have also discovered a method for identifying nucleic acid sequences of components involved in the signal transduction pathway between branched chain amino acid biosynthetic pathways and nuclear gene expression.

Chimeric Constructs and Plant Transformation

In the present invention, applicant utilizes a reporter system as a tool to analyze gene activity in genetically altered plants. The chief components of this reporter system are a gene encoding a reporter and a promoter that is operably linked to such gene.

As used herein a "reporter gene" is a coding region which when expressed displays an easily assayed and novel phenotype or biochemistry in the plant, thus, reporting on the activity of the promoter to which it is operably linked. Preferred reporter genes used in the reporter systems of the present invention include CAT (chloramphenicol acetyl transferase), Gus (B-glucuronidase), green fluorescent protein, and luciferase. These enzymes are particularly useful because their activities are rather easily assayed for in crude plant extracts. Further, their activity can be measured by incubating a substrate with a cell extract from the transformed plant expressing the reporter. Products can be assayed spectrophotometrically, fluorescently, radioactively or other like manner. It should be noted that this is not an exhaustive list of reporter genes that may be utilized in the plant reporter systems of the present invention and one skilled in the art of molecular genetics could readily design a reporter system employing other reporters. Preferably, to maximize its effectiveness reporter genes used in the present system preferably do not normally have endogenous activity in plant tissue (or have endogenous activity which can be blocked) so there is not a problem distinguishing the reporter activity from background activity.

In a preferred embodiment of the present invention the luciferase reporter gene has been selected for inclusion in the reporter system. Luciferase was chosen as the reporter because luciferase activity can be monitored in vivo without affecting the integrity of the plant. For example, luciferase activity can be detected in imaging experiments employing a photon-counting CCD camera system. This feature opens up the possibility to perform rapid examination of many plants as well as to reexamine the same tissue several times throughout an experiment (Millar et al., (1992) Plant Mol. Biol. Rep. 10, 324–337). The in Plantae pool of luciferase protein can be inactivated by treatment with luciferin. This facilitates the study of luciferase transcription and translation over a defined time period, regardless of the luciferase pool present before treatment with luciferin (Millar et al., 1992). Also, luciferase activity can easily be reexamined in vitro providing the means for fast confirmation of results obtained by in vivo monitoring.

A second key component to the reporter system of the present invention is the promoter selected to drive expression of the reporter gene. Promoters are untranslated sequences located generally 100 to 1000 base pairs (bp) upstream from the start codon of a structural gene that regulate the transcription and translation of nucleic acid sequences under their control. Promoters are generally either inducible or constitutive under a defined growth condition. Inducible promoters are promoters that initiate increased levels of transcription from DNA under their control in response to some change in the environment, e.g., the presence or absence of a nutrient or a change in temperature. Constitutive promoters, in contrast, maintain a relatively constant level of transcription. In addition, useful promoters can also confer appropriate cellular and temporal specificity. Such inducible promoters include those that are developmentally-regulated or organelle-, tissue- or cell-specific.

Preferably a promoter that controls expression of the reporter gene in response to relevant conditions is used in the instant reporter system. Accordingly, in a preferred embodiment of the present invention, a portion of the gene encoding an AOX promoter for Arabidopsis, AOX1a, is included in a preferred embodiment of the reporter system. The nucleotide sequence for the portion of AOX1a included in a preferred embodiment of the present invention is provided herein as SEQ ID NO:4. Applicant has discovered that the AOX1a promoter is inducible in response to a number of stimuli whereby communication of mitochondrial status to nuclear gene expression is implicated and causes an increase in reporter gene transcription. Additionally, the AOX1a reporter system also provides a method to identify components involved in the signal transduction pathways between branched chain amino acid biosynthetic pathways and nuclear gene expression (Aubert et al., (1997) Plant J. 11:649–657). Detection of alteration of AOX1a activity by a reporter system in mutant plants in response to these stimuli provides a novel method to elucidate key components of the mitochondrial function and metabolic status to nuclear signal transduction pathway and the pathways between branched chain amino acid biosynthetic pathways and nuclear gene expression.

The nucleic acid sequence for the promoter region of the AOX gene that is induced in responses to chemical treatment contains highly conserved sequence regions across plant species. As evidenced by both structural and functional studies characterizing AOX promoters. For example, an AOX gene has been shown to have a conserved element in the promoter region in Arabidopsis, soy bean, and voodoo lily (Finnegan et al., (1998) Plant Mitochondria: From Gene to Function 449–453). In addition to sequence homology, an AOX promoter also exhibits functional conservation across plant species. Based on the discovery documented herein showing increased accumulation of AOX1a transcript following AA treatment of Arabidopsis plants is due to increased transcription, it can be surmised that analogous AOX promoters direct the increases in AOX protein and transcript observed in response to application of antimycin A, an inhibitor of complex III of the cyctochrome mtETC pathway, in petunia cells, tobacco, and *Hensenula anomala* (Vanlerberghe et al., (1994) Plant Physiol. 105:867–874; Saisho et al., (1997) Plant Mol. Biol. 35:585–596; Minagawa et al., (1992) FEBS Lett. 302:217–219; and Aubert et al., (1997) Plant J. 11:649–657). The transcript of an AOX gene has also been shown to accumulate in response to application of salicylic acid in *Sauromatum guttatum* and tobacco (Rhoads et al., (1992) Plant Cell 4:1131–1139; Kapulnik et al., (1992) Plant Physiol. 100:1921–1926; and Rhoads et al., (1993) Plant Physiol. 103:877–883). Additionally, AOX mRNA accumulates in response to inhibitors of branched-chain amino acid biosynthesis in cultured sycamore cells (Aubert et al., (1997) Plant J. 11:649–657). Additionally, AOX mRNA has been shown to accumulate in response to an increase in the amount of citrate in tobacco cells (Vanlerberghe et al., (1996) Plant Physiol. 111:589–595). Hence, AOX accumulates in numerous plant species in response to inhibition of the cytochrome mtETC pathway and metabolic perturbations. Thus, the AOX promoter exhibits both functional and structural homology across a variety of plant species.

In fact it has been extensively demonstrated that plant promoters function in other plant species, which demonstrates the conservation of the mechanisms and sequences that allow promoters to respond to various stimuli. For example, it has been shown that the promoter for the wheat chlorophyll a/b-binding protein gene cab-1 (a gene known to be controlled by circadian rhythm in all plants investigated so far) is controlled by circadian rhythm when introduced into tobacco plants by transformation [Nagy F, Kay SA & Chua N.-H. (1988) Genes Dev. 2: 376–382]. Secondly, the 35S promoter of the cauliflower mosaic virus directs constitutive expression of genes in tobacco and Arbidopsis. It was also demonstrated that a methyl jasmonate-inducible promoter of the potato gene encoding a protein called inhibitor II was also induced by methyl jasmonate in transgenic tobacco plants [Thornburg R W, An G, Cleveland T E, Johnson R & Ryan C A (1987) PNAS 84; 744–748]. These are just a few of the many examples that demonstrate the conservation of the functional regions of promoters in plants.

As detailed above, sequence for a promoter region of an AOX gene, AOX1a, from Arabidopsis has been isolated. The DNA sequence has been determined and is given in SEQ ID NO: 4. Although a particular embodiment of the nucleotide sequence disclosed herein is given in SEQ ID NO: 4, it should be understood that other biologically functional equivalent forms of the nucleic acid sequence of the present invention can be readily isolated using conventional DNA-DNA and DNA-RNA hybridization techniques. Thus the present invention also includes nucleotide sequences that hybridize to SEQ ID NO: 4 or its complement under moderate to high stringency conditions. Also included in the invention are polynucleotides that exhibit 90%, preferably 92%, more preferably 95%, and more 98% sequence identity with SEQ ID NO: 4, or its complement. Such nucleotide sequences preferably hybridize to the nucleic acid of SEQ ID NO: 4 or its complement under high stringency conditions. Exemplary conditions include initial hybridization in 5×SSPE,1–5×Denhardt's solution, 10–200 µg/ml denatured heterologous DNA, 0.5% SDS, at 50–68° C. for a time sufficient to permit hybridization, e.g. several hours to overnight, followed two washes in 2×SSPE, 0.1% SDS at room temperature and two additional 15 minute washes in 0.1×SSPE, 0.1% SDS at 42° C. followed by detection of the hybridization products. Higher stringency washing can accomplished by at least one additional wash in 0.1% SSPE, 0.1% SDS at 55° C., more preferably at 60° C. and more preferably still at 65° C. High stringency hybridizations can also be carried out in 5×SSPE and 50% formamide at 42° C. followed by washing as described above (Meinkoth and Wahl, *Anal. Biochem,* 138:267–284 (1984)). As is well known by those of ordinary skill in the art, SSC can be substituted for SSPE in the above examples so that, for instance, hybridization can be accomplished in 5×SSC in place of 5×SSPE.

It is well known to those of ordinary skill in the art that different compositions can result in equal stringency conditions for hybridization depending on well known factors such as the concentration of $Na^+$, the % formamide, the temperature, the $T_m$ of the hybrid to be formed, and the composition of the hybrid, e.g. DNA-DNA, DNA-RNA, or RNA-RNA. Thus the invention also encompasses nucleotide sequence that hybridize under conditions equivalent to those described above.

In order to construct the binary vector for a preferred embodiment of the present invention, a portion of the promoter region from the AOX gene was subcloned as set-forth in greater detail in the examples below. The subcloned portion of AOX utilized in construction of the vector is set-forth herein as SEQ ID:4. The subcloning can be accomplished using a variety of procedures commonly known to those skilled in the art and detailed in, for example, Sambrook et al., Molecular Cloning, A Laboratory Manual, 2nd ed., Cold Spring Harbor Laboratory Press, (1989) and Ausabel et al., Short Protocols in Molecular Biology, 3rd. ed., John Wiley & Sons (1995). Additionally, in the described embodiment, the subcloned portion of the AOX gene was then inserted into the binary vector as set-forth in greater detail in the examples below. The nucleotide sequence may be inserted into the vector by a variety of methods. In a preferred method the sequence is inserted into an appropriate restriction endonuclease site(s) using procedures commonly known to those skilled in the art and detailed in, for example, Sambrook et al., *Molecular Cloning, A Laboratory Manual,* 2nd ed., Cold Spring Harbor Laboratory Press, (1989) and Ausubel et al., *Short Protocols in Molecular Biology,* 3rd ed., John Wiley & Sons (1995).

In a the preferred embodiment of the present invention the vector is transformed into Arabidopsis by agrobacterium-mediated DNA transfer (Zupan et al., (1995) Plant Physiol. 107:1041–47). The bacterium contains a large plasmid called the Ti plasmid with genes that alter plant hormone production. The genes responsible for abnormal growth are located on a portion of the Ti plasmid called T-DNA, which is transferred to the plant chromosome after infection by the bacteria. The Ti plasmid has been engineered to enhance its usefulness for plant transformation. This engineered plasmid is known as a binary T-DNA plasmid vector (binary vector). The binary vector contains restriction sites to allow insertion of a gene of interest, a selectable marker (often an antibiotic resistance gene) and often an origin of replication which allows the vector to be replicated in *E. coli* as well as agrobacterium. The binary vector cannot infect the plant by itself so it must be introduced into an agrobacterium strain that also carries a second Ti plasmid. This second plasmid does not contain T-DNA, but does contain the genes which allow the agrobacterium to infect plant cells and to transfer T-DNA from the binary plasmid.

The nuances of agrobacterium-mediated DNA transfer are commonly known to those skilled in the art (Zupan et al., (1995) Plant Physiol. 107:1041–47). Other methods to transform plants may be utilized and are known to those skilled in the art including but not limited to: 1) the particle gun method (Gordon-Kamm et al., (1990) Plant Cell 2:603–618); 2) the PEG method (Zhang et al., (1988) Theor. Appl. Genet. 76:835–840); 3) culturing seeds or embryos with DNA (Topfer et al., (1989) Plant Cell 1:133–139); 4) microinjection method (Neuhaus et al., (1987) Theor. Appl. Genet. 75:30–36); and 5) the electroporation method (Toriyama et. al., (1988) Biol. Technol. 6:1072–1074).

Identification of Transgenic Plants

Plants are screened for presence of the binary construct by assaying for the presence of the luciferase or other reporter gene as set-forth in greater detail below in the examples. In a preferred embodiment of the present invention, however, a photon counting, CCD imaging camera is utilized to quantify the levels of AOX promoter-driven luciferase expression in response to various stimuli such as inhibition of either the cytochrome mETC pathway or branched chain amino acid biosynthesis.

Application of the stimuli is optimized in order to ensure that plants are able to survive the screening process. Only transgenic plants in the homozygous state are selected. Homozygous plants may be determined on the basis of resistance to kanamycin (antibiotic selectable marker present in the binary vector) and a homozygote, when allowed to self pollinate will not produce any progeny that are kanamycin sensitive. The antibiotic resistance conferred as a result of the vector's incorporation into the plant's genome, thus, provides a method to ensure that plants are homozygous.

Mutagenesis of Transgenic Plants

In a preferred embodiment of the current invention, seeds collected from transgenic plants that express the luciferase reporter gene at normal levels in response to the application of stimuli are mutagenized using either ethylmethane sulfonate (EMS) or T-DNA insertion mutagenesis (Feldman K., Methods in Arabidopsis Research, World Scientific Co., (1992); and Redei et al., Classical mutagenesis, In Methods in Arabidopsis Research, World Scientific Co., (1992)). EMS mutagenesis is typically favored over T-DNA mutagenesis because: a) EMS mutagenesis is technically more straightforward in producing the mutations and the average number of mutations in one given seed is well controlled. This allows for a quick assessment; b) EMS mutagenesis tends to generate more types of mutations in a single gene, thus producing more mutant alleles. This means that EMS is likely to produce more proteins with slightly altered properties, whereas T-DNA insertion tends to completely eliminate expression when inserted into the coding region or alter transcription levels if inserted outside of the coding region, but alter proteins identified in the screening; c) T-DNA insertion can affect expression of genes that are not near the insertion site and can cause chromosomal deletions; d) although finding a T-DNA tagged gene is technically easier, methods for finding EMS mutated genes is rapidly advancing with the sequencing of the Arabidopsis genome. Preferably, the general effectiveness of the mutagenesis procedure is determined as suggested by Redei and Koncz (Rédei et al., Classical mutagenesis, In Methods in Arabidopsis Research, World Scientific Co., (1992)). It should be noted that other parts of the plant or other mutagens, such as transposable element insertion, also may be employed for mutagenesis.

In a preferred embodiment, mutagenized seeds are plated on agar in petri plates in defined grid patterns. In this procedure, to destabilize the existing luciferase molecules, plants are treated with a luciferin solution twice, two days prior to screening and once the day before screening. On the day of screening, plants are treated with a luciferin solution and imaged in both the light and darkness (measuring luminescence for luciferase) in a photon counting, CCD camera at time zero and then treated with antimycin A or sulfometuron methyl (inhibitor of branched-chain amino acid biosynthesis). Six to 24 hours later, depending on the peak response times under the treatment conditions, the plants are again imaged. In a preferred embodiment, plants are selected with no expression of luciferase, lower expression than controls, and higher expression than controls. Each of these categories of plants are considered mutants affected in control of expression of AOX and are candidates for further analysis.

Preferably, any mutant obtained through a screen with one treatment is tested for its response to the other treatments. For example, if a mutant were identified as responding to antimycin A treatment with altered luciferase transgene expression and endogenous AOX transcript accumulation, it will also be tested for its response to salicylic acid, sulfometuron methyl, and citrate.

Mutants may be checked to make sure they are not just mutated in the AOX promoter::luciferase transgene by RNA blot analyses using an AOX gene-specific probe to verify that there is altered expression of the endogenous AOX gene. True mutants will, in response to the stimuli used in the screen (i.e. antimycin A, sulfometuron methyl, salicylic acid, or citrate treatment), show either no, lower, or elevated AOX transcript accumulation relative to control plants.

Antimycin A and sulfometuron methyl enter into leaf cells readily and likely cross membranes without the need for transporters, therefore there is little chance that the response mutants will be just "uptake mutants." It is possible, though unlikely, that a mutation could alter the specificity of an endogenous enzyme such that it detoxifies the antimycin A or sulfometuron methyl before they reach the sites of action. It is also possible that mutants of acetolactate synthase or complex III that are no longer inhibited by sulfometuron methyl or antimycin A, respectively, will be isolated. In any event, to eliminate these possibilities, altered luciferase expression in the antimycin A response mutants may be demonstrated using other inhibitors of the mtETC that act at other sites, such as cyanide (an inhibitor of cytochrome oxidase) or myxothiazol (an inhibitor of another site in complex III). Altered luciferase expression of the sulfometuron methyl response mutants using inhibitors of acetolactate reductoisomerase also may be determined.

Identification of a Mutant Gene From A Transgenic Plant

In one method of the invention, as mutants are isolated, the mutant genes are identified by mapping their positions in the Arabidopsis chromosomes. Genomic DNA is isolated from homozygous mutant plants using CAPS (cleaved amplified polymorphic sequences) RAPD (random amplified polymorphic DNA) and SSLPs (simple-sequence length polymorphism) as markers to determine the chromosome position (Reiter et al., Genetic linkage of the Arabidopsis genome: methods for mapping with recombinant inbreds and random amplified polymorphic DNAs (RAPDs) In Methods in Arabidopsis Research, World Scientific, (1992)). Once the location of the mutant gene has been narrowed to between two markers, bacterial artificial chromosome (BAC) libraries and yeast artificial chromosome (YAC) libraries containing Arabidopsis chromosomal fragments and genomic sequence information may be used to isolate the mutated genes (Gibson et al., Chromosome walking in *Arabidopsis thaliana* using Yeast Artificial Chromosomes, In Methods in Arabidopsis Research, World Scientific Co., (1992)).

In another embodiment, cDNA micro array technology is employed to elucidate alterations of gene expression in mutant plants relative to control plants (Harmer et al., (2000) Plant Cell 12:613–616). In micro array, cDNA representing a portion of the genome of the plant under study (or EST sequences) is deposited on a glass. The cDNA made from mRNA isolated from various mutant and control populations are differentially labeled (for example, by a fluorescent label) and allowed to hybridize with the reference cDNA. After hybridization, a high resolution scanner quantifies the results. Thus, micro array efficiently and globally characterizes patterns of gene expression in the mutant plants relative to the control population.

Isolation of Mitochondrial and Nuclear Proteins

Preferably, after determining the sequence of the genes involved in the signal transduction pathway, as set forth above, the proteins that such genes encode are identified by searching sequence databases for EST clones already known to encode both mitochondrial and nuclear proteins by various strategies including a) searching the protein names, and b) searching data bases for protein sequences obtained from direct sequencing of plant mitochondrial proteins and cDNA sequences, genomic sequences, and EST sequences from both mitochondrial and nuclear protein clones from other organisms, especially yeast.

The detailed description set-forth above is provided to aid those skilled in the art in practicing the present invention. Even so, this detailed description should not be construed to unduly limit the present invention as modifications and variation in the embodiments discussed herein can be made by those of ordinary skill in the art without departing from the spirit or scope of the present inventive discovery.

All publications, patents, patent applications and other references cited in this application are herein incorporated by reference in their entirety as if each individual publication, patent, patent application or other reference were specifically and individually indicated to be incorporated by reference.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

Example 1

Construction of the PZB-ALN and PZP-ALE Vectors

Figure 2:
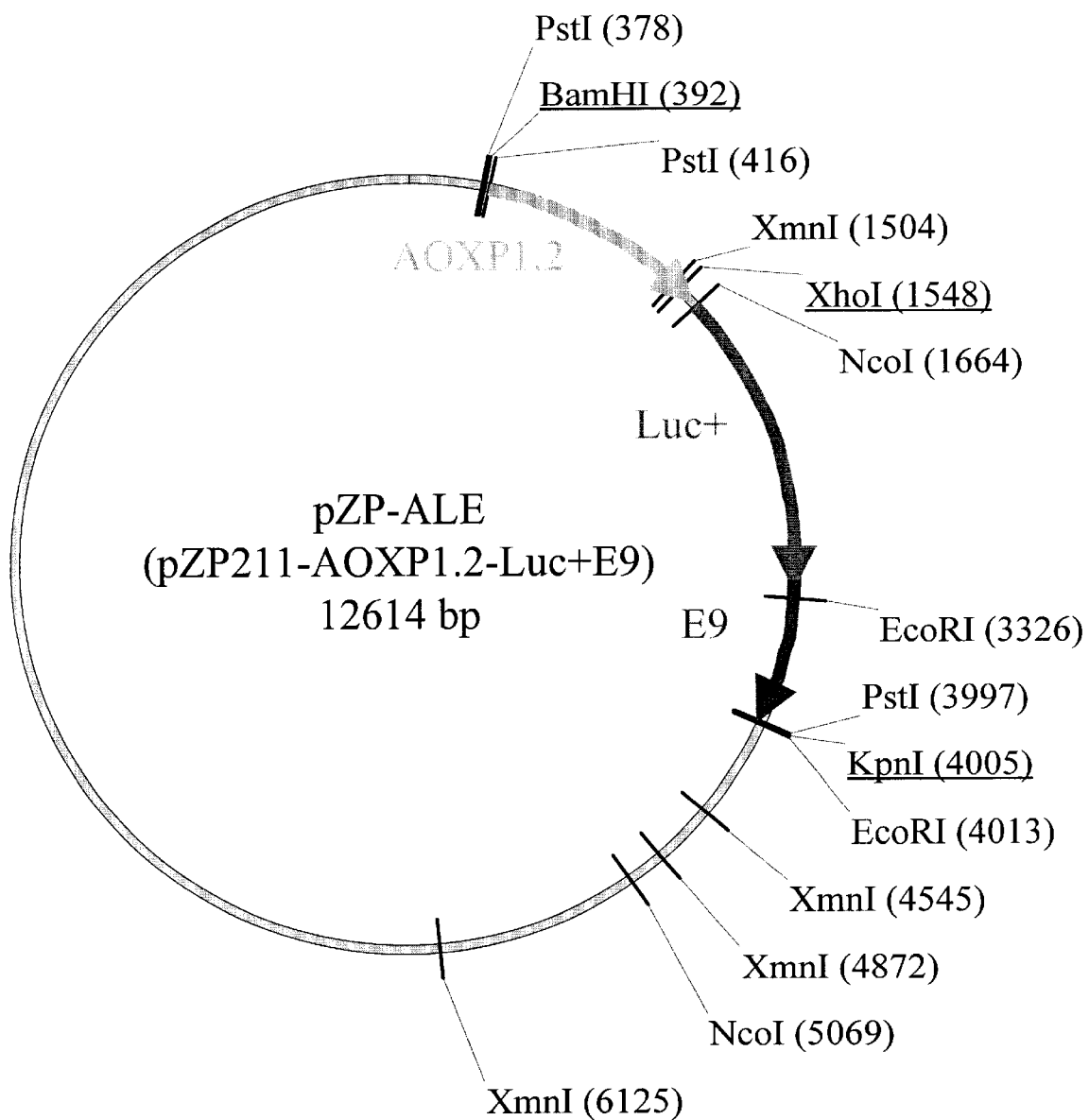
FIG. 2 shows the vector map for PZP-ALE. The promoter of gene AOX1a (indicated as AOXP1.2), luciferase (indicated as Luc+) and E9 coding regions are represented by arrows, and important restriction sites are shown. The nucleotide sequence is provided herein as SEQ ID NO:1.
Figure 3:
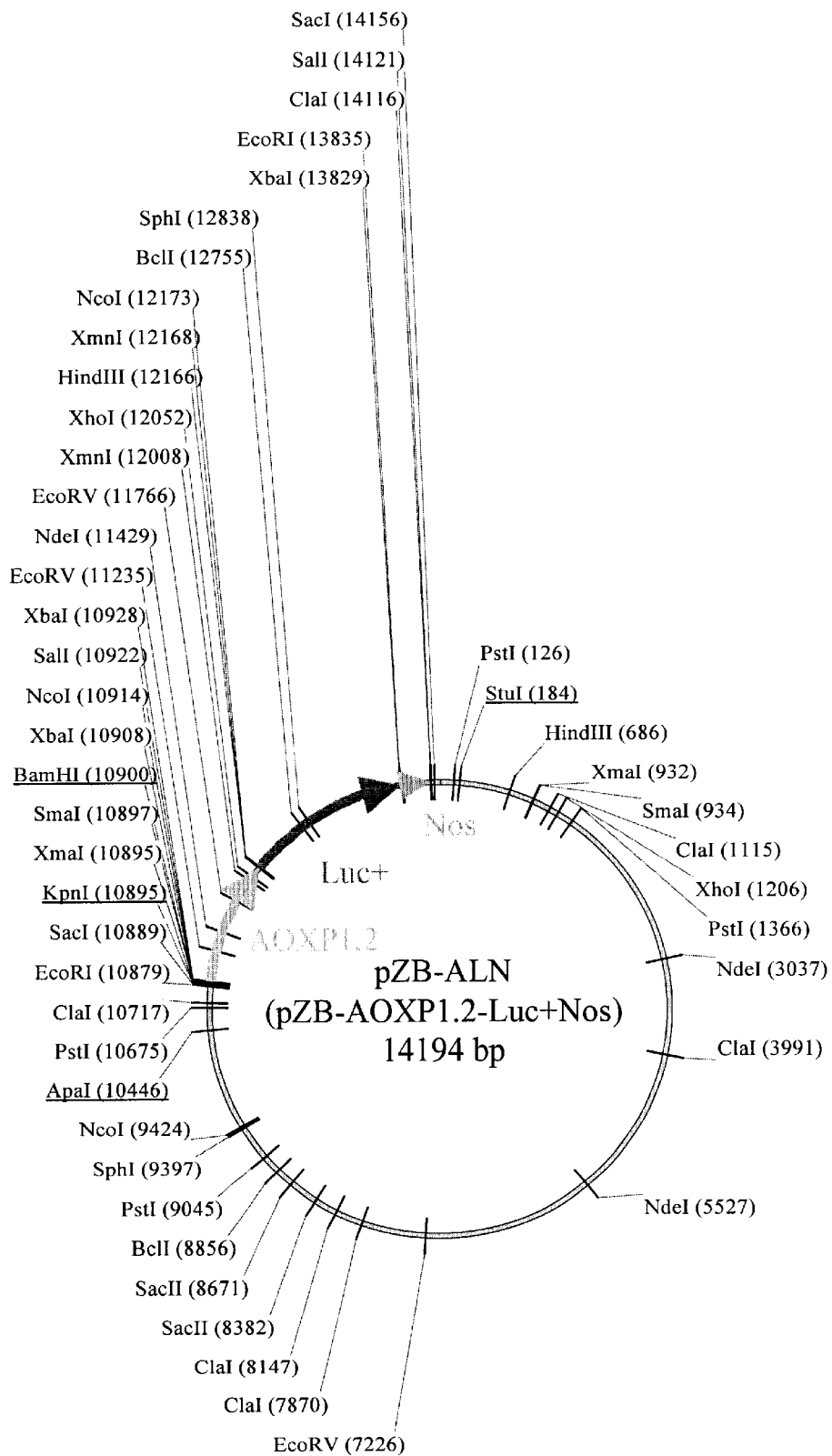
FIG. 3 shows the vector map for pZB-ALN. The AOX, AOX1a, promoter (indicated as AOXP1.2), luciferase (indicated as Luc+) and Nos coding regions are represented by arrows. The nucleotide sequence is provided herein as SEQ ID NO:3.

Two binary vector constructs were created referred to as pZP-ALE and pZB-ALN (see FIG. 2 SEQ ID NO:1; and FIG. 3 SEQ ID NO:3 respectively). The initial steps in the construction were the same for both vectors as detailed herein. The promoter fot the gene encoding Arabidopsis AOX1a gene was subcloned and the sequence utilized for construction of the vectors is set-forth herein as SEQ ID NO:4. PCR was performed in order to add Bgl II and Nco1 restriction sites to the AOX1a promoter sequence. The primers utilized in the PCR reaction were 5'-CCA TAG ATC TGT CCA TTA AAC CCC AC-3' (SEQ ID NO:5) to add the Bgl ll restriction site and 5'-GTT ATC ACC ATG GTT TCA AAT CGG-3' (SEQ ID NO:6) to add the Nco1 restriction site. The PCR products were then restriction digested with Bgl ll and Nco1 and ligated into a similarly digested pUC120 vector. This construct is referred to as pUC120-AOXP.

The pUC120-AOXP vector was subsequently restriction digested with Hind III and Nco I and the ends were filled in. The digestion product was then blunt end ligated into pBluescript KS+in the Sma I site and the resulting vector is referred to as pBSKS+AOXP. The pBSKS+AOXP vector was engineered such that the Nco I site at the 3' end was regenerated.

pZP-ALE Construction

The pBSKS+AOXP vector was restriction digested with BamHI and HindIII. The digestion product was then subcloned into the pZP221-Omega-Luc+E9 and the resulting vector is referred to as pZP221-AOLE. The AOX promoter is in front of Omega.

The pZP221-AOLE vector was then digested with Bam H1 and Sac I and subcloned into a similarly digested pBluescriptKS+ vector. This construct is referred to as pBSKS+AOLE. This vector is then digested with Nco I and then subsequently ligated together again. This step removes the Omega site, which can impede expression. The vector without the Omega is referred to as pBSKS+ALE.

Vector pBSKS-ALE was subjected to restriction difestion with BAM H1 and KpnI and then inserted in to a similaryly digested pZP211 vector. The resulting vector is referred to as pZP-ALE. This construct is a binary vector and contains the AOX promoter (as detailed above) operably linked to a luciferase gene with an E9 polyadenylation signal sequence/transcriptional terminator at the 3' end. The vector was employed to transform plants as set forth in example 2.

pZB-ALN Construction

The pUC120-AOXP vector was digested with Bam H1 and Nco1 (the Bam H1 site was created as a result of inserting the PCR product detailed above into pUC120). The digestion product was subcloned into a vector pBluescriptKS+ engineered to express Luc+-Nos. The resulting vector is referred to as pBSKS+ALN.

The pZP-ALE and pZB-ALN vectors were both restriction mapped and sent for DNA sequencing in order to ensure insertion of all constructs set-forth above.

Example 2

Identification of Transgenic Plants With Altered Expression of Luciferase

Figure 4:
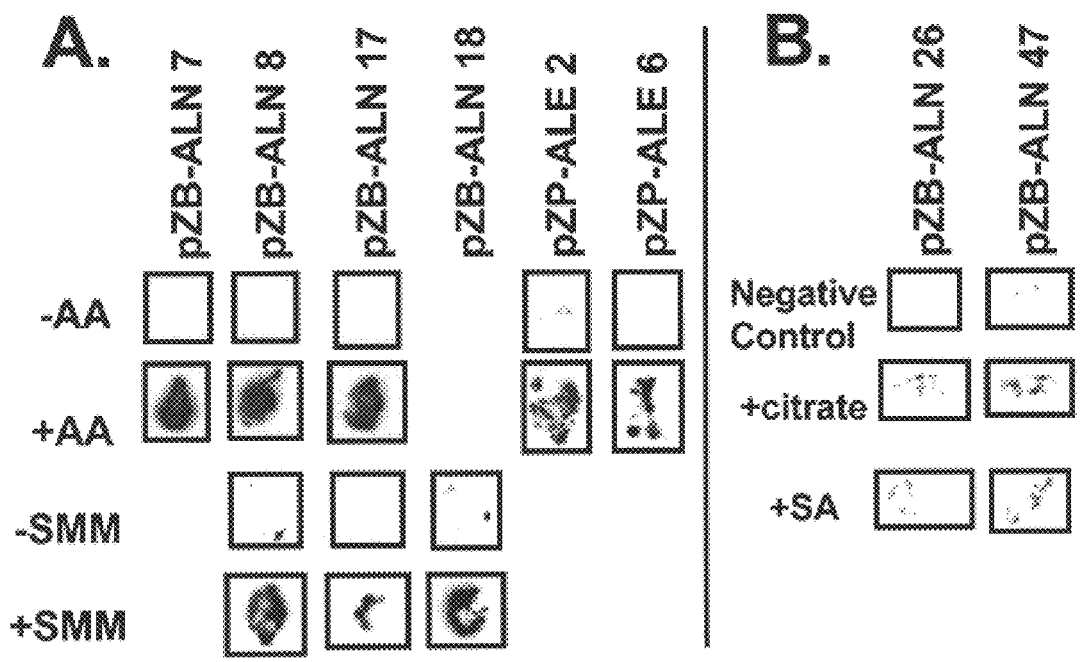
FIGS. 4A and 4B depict luciferase activity in transgenic plants subjected to the treatment indicated as measured by exposure to film employing either the pZB-ALN vector or the pZP-ALE vector.

Initial screening of the F1 plants was done by spraying excised leaves with 10 uM AA (FIG. 4A). The leaves were incubated for 4 hr in the light, then sprayed with luciferin, and exposed to autoradiographic film. Several of the transgenic Arabidopsis lines showed a strong response to antimycin A (FIG. 4A). Leaves from pZB-ALN lines 7, 8, 17 (FIG. 4A), 4, 5, 6, 9, 10, 11, 15, 16, 18, 26 and 47 (data not shown) and pZP-ALE lines 2 and 6 (FIG. 4A) qualitatively exhibited higher luciferase expression 4 h after treatment with 10 uM antimycin A than did untreated control leaves (FIG. 4A). Some of these lines also exhibited higher luciferase expression 24 h following treatment with 5 nM sulfometuron methyl (FIG. 4A). In addition, lines PZB-ALN 26 and 47 showed a lower, but definite response to citrate or salicylic acid application (FIG. 4B). Several pZB-ALN lines were used for imaging experiments employing a Hamamatsu photon-counting, CCD camera system (model C2400-75H).

Figure 6:
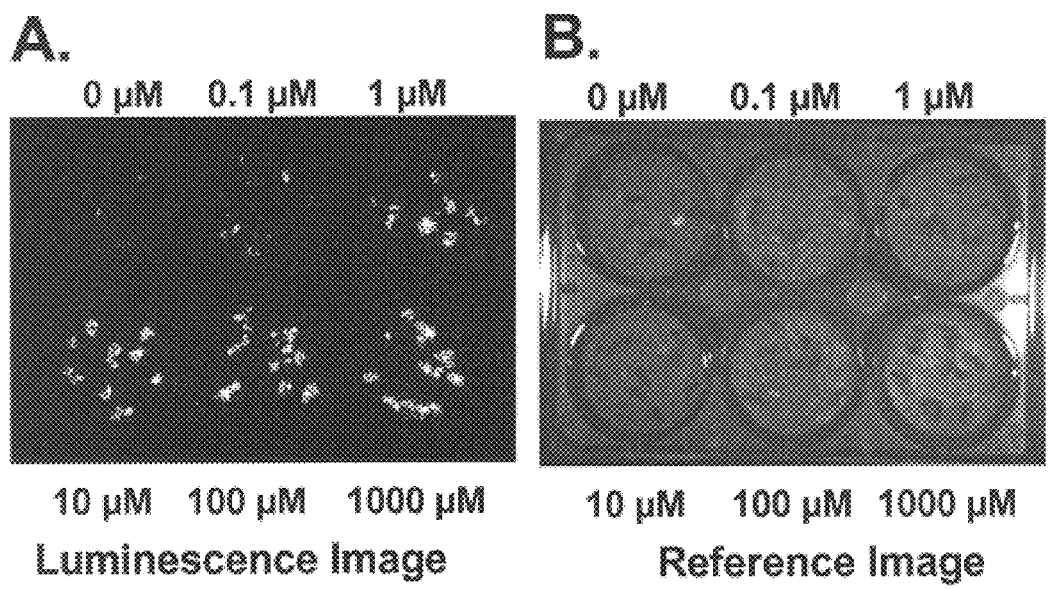
FIG. 6 depicts luciferase expression from PZB-AIN induced by AA.
Figure 6:
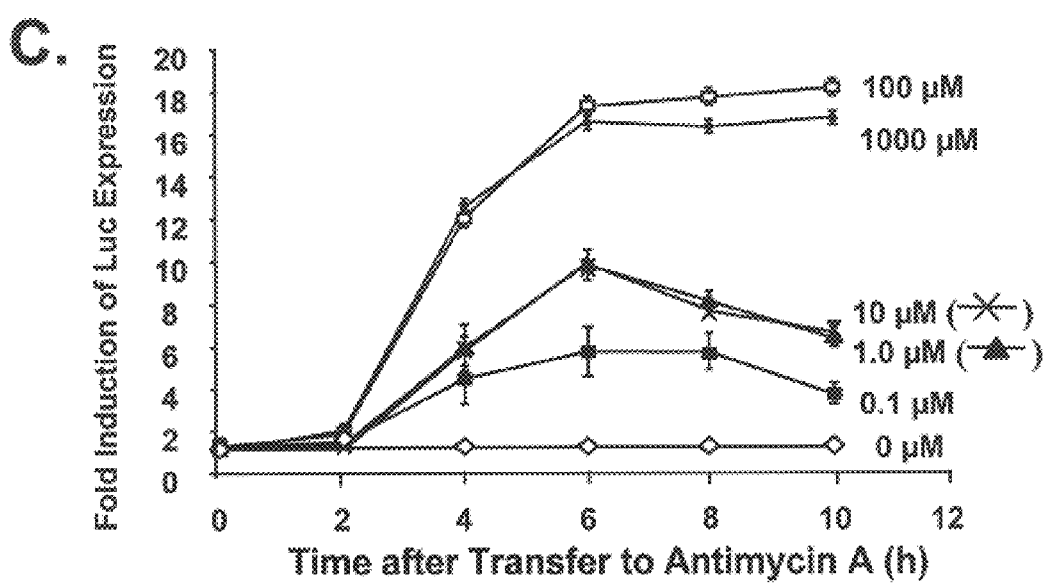

Based upon initial experiments, lines pZB-ALN 8 and pZB-ALN 17 were selected for further analyses. Seeds from these lines were sterilized and germinated on filter discs on standard growth agar in six-well plates and then grown at 20° C. and 66 uE of continuous light for 7 days (to eliminate the possibility of circadian rhythm effects). A Hamamatsu CCD camera system was used to quantify the levels of AOXP-driven luciferase expression. For the dose-response experiments (FIG. 6), plants on the filter disks were transferred to six-well, induction plates in which each well contained a unique concentration of antimycin A. Plants were imaged immediately following transfer to induction plates, then returned to the growth chamber under 66 uE continuous light and 20° C. Imaging was again done at 2, 4, 6, 8, and 10 h after transfer to induction plates. Luciferase expression controlled by the AOXP, when induced by 1.0 mM or 100 uM antimycin A, reaches a peak of about 17-fold induction over the negative control at about 6 h after application of antimycin A in line pZB-ALN 8 and stays at this level until at least 10 h after transfer (FIG. 6B). This level of induction is easily detected by the Hamamatsu CCD camera (FIG. 6A). Although 1.0 mM or 100 uM antimycin A application consistently resulted in the highest induction levels, measurable induction resulted from concentrations as low as 0.1 uM (FIG. 6). Similar results were obtained using transgenic Arabidopsis line pZB-ALN17 (data not shown). The induction followed the same time-course as for pZB-ALN 8.

Figure 5:
FIG. 5 depicts the ability of Arabidopsis seedlings to survive treatment at the AA concentrations indicated.
Figure 5:
Figure 5:

In order for a screen involving application of antimycin A or sulfometuron methyl to succeed, plants must survive the screening procedure. It has been demonstrated that Arabidopsis plants can survive antimycin A treatment (FIG. 5). Plants from line pZB-ALN 8 were used to produce the dose response curve shown in FIG. 6 were transferred to fresh growth plates (without antimycin A) after 36 h of antimycin A treatment. Plants treated with each concentration of antimycin A tested (0.1, 1.0, 10, 100, and 1000 uM) survived without any apparent developmental alterations for six days after treatment (FIG. 5). These plants remained green with healthy, expanded first true leaves and healthy roots and produced a normal-looking second set of true leaves. Also, wild-type Arabidopsis plants sprayed with 5 uM or 5 nM sulfometuron methyl survive treatment (data not shown).

These results establish that the unique reporter method detailed herein will identify components involved in the signal transduction pathways between mitochondrial and nuclear gene expression in higher plants. In addition, these results establish that the unique reporter method detailed herein will identify components involved in the signal transduction pathways between branched chain amino acid biosynthetic pathways and nuclear gene expression. In view of the above, it will be seen that the several objectives of the invention are achieved and other advantageous results attained.

What is claimed is:

1. A method for identifying the nucleic acid sequence of a gene encoding a protein that participates in a signal transduction pathway between mitochondrial function and nuclear gene expression in *Arabidopsis thaliana* comprising:
   (a) transforming the *Arabidopsis thaliana* with a vector, the vector comprising a gene that encodes a reporter protein operably linked to an *Arabidopsis thaliana* AOX1a promoter consisting essentially of a nucleic acid sequence of SEQ ID NO:4 or the complement thereof;
   (b) identifying a transgenic *Arabidopsis thaliana* from step a that increases the expression of the gene encoding the reporter protein when subjected to a stimulus relative to the basal level of endogenous expression of the gene;
   (c) mutating the transgenic *Arabidopsis thaliana* identified in step b;
   (d) selecting a mutant transgenic *Arabidopsis thaliana* from step c, wherein the mutant *Arabidopsis thaliana* exhibits altered expression of the gene encoding the reporter protein relative to an unmutagenized *Arabidopsis thaliana*;
   (e) determining the nucleic acid sequence of the gene that encodes the protein that participates in the signal transduction pathway in the mutant *Arabidopsis thaliana* from step d.

2. The method of claim 1, wherein the reporter protein is selected from the group consisting of luciferase, B-glucuronidase, green fluorescent protein, chloramphenicol acetyl transferase, red fluorescent protein, and blue fluorescent protein.

3. The method of claim 2, wherein the reporter protein is luciferase.

4. The method of claim 1, wherein the stimulus is a mitochondrial electron transport inhibitor.

5. The method of claim 4, wherein the mitochondrial electron transport inhibitor is selected from the group consisting of antimycin A, myxothiazol, cyanide rotenone, and carbon monoxide.

6. The method of claim 5, wherein the mitochondrial electron transport inhibitor is antimycin A.

7. The method of claim 1, wherein the stimulus is metabolic perturbation.

8. The method of claim 1, wherein the stimulus is salicylic acid.

9. The method of claim 1, wherein the stimulus is an increase in citrate concentration.

10. The method of claim 1, wherein the mutating is accomplished by treatment with ethylmethane sulfonate.

11. The method of claim 1, wherein the mutating is accomplished by T-DNA insertion.

12. The method of claim 1, wherein the mutating is accomplished by transposable element insertion.

13. The method of claim 1, wherein the vector comprises SEQ ID NO:1.

14. The method of claim 1, wherein the AOX1a promoter and the gene encoding the reporter protein form a polynucleotide of bases 361 through 3317 of either SEQ ID NO:1 or SEQ ID NO:3.

15. A method for identifying the nucleic acid sequence of a gene encoding a protein that participates in a signal transduction pathway between branched chain amino acid biosynthetic pathways and nuclear gene expression in *Arabidopsis thaliana* comprising:
   (a) transforming the *Arabidopsis thaliana* with a vector, the vector comprising a gene that encodes a reporter protein operably linked to an *Arabidopsis thaliana* AOX1a promoter consisting essentially of a nucleic acid sequence of SEQ ID NO:4 or the complement thereof;
   (b) identifying a transgenic *Arabidopsis thaliana* from step a that increases the expression of the gene encoding the reporter protein when subjected to a stimulus relative to the basal level of endogenous expression of the gene;
   (c) mutating the transgenic *Arabidopsis thaliana* identified in step b;
   (d) selecting a mutant transgenic *Arabidopsis thaliana* from step c, wherein the mutant *Arabidopsis thaliana* exhibits altered expression of the gene encoding the reporter protein relative to an unmutagenized *Arabidopsis thaliana*;
   (e) determining the nucleic acid sequence of the gene that encodes the protein that participates in the signal transduction pathway in the mutant *Arabidopsis thaliana* from step d.

16. The method of claim 15, wherein the reporter protein is selected from the group consisting of luciferase, B-glucuronidase, green fluorescent protein, chloramphenicol acetyl transferase, red fluorescent protein, and blue fluorescent protein.

17. The method of claim 16, wherein the reporter protein is luciferase.

18. The method of claim 15, wherein the mutating is accomplished by treatment with ethylmethane sulfonate.

19. The method of claim 15, wherein the mutating is accomplished by T-DNA insertion.

20. The method of claim 15, wherein the mutating is accomplished by transposable element insertion.

21. The method of claim 15, wherein the vector comprises SEQ ID NO:1.

22. The method of claim 15, wherein the AOX1a promoter and the gene encoding the reporter protein form a polynucleotide of bases 361 through 3317 of either SEQ ID NO:1 or SEQ ID NO:3.

23. The method of claim 15, wherein the stimulus is metabolic perturbation.

24. A method for identifying the nucleic acid sequence of a gene encoding a protein that participates in a signal transduction pathway between mitochondrial function and nuclear gene expression in *Arabidopsis thaliana* comprising:

(a) transforming the *Arabidopsis thaliana* with a vector, the vector comprising a gene that encodes a luciferase protein operably linked to an *Arabidopsis thaliana* AOX1a promoter consisting essentially of a nucleic acid sequence of SEQ ID NO:4 or the complement thereof;

(b) identifying a transgenic *Arabidopsis thaliana* from step a that increases the expression of luciferase when subjected to a stimulus relative to the basal level of endogenous expression of the gene;

(c) mutating the transgenic *Arabidopsis thaliana* identified in step b;

(d) selecting a mutant transgenic *Arabidopsis thaliana* from step c, wherein the mutant *Arabidopsis thaliana* exhibits altered expression of the luciferase gene relative to an unmutagenized *Arabidopsis thaliana*;

(e) determining the nucleic acid sequence of the gene that encodes the protein that participates in the signal transduction pathway in the mutant *Arabidopsis thaliana* from step d.

25. The method of claim 24, wherein the stimulus is a mitochondrial electron transport inhibitor.

26. The method of claim 25, wherein the mitochondrial electron transport inhibitor is selected from the group consisting of antimycin A, myxothiazol, cyanide rotenone, and carbon monoxide.

27. The method of claim 26, wherein the mitochondrial electron transport inhibitor is antimycin A.

28. The method of claim 24, wherein the stimulus is metabolic perturbation.

29. The method of claim 24, wherein the stimulus is salicylic acid.

30. The method of claim 24, wherein the stimulus is an increase in citrate concentration.

31. The method of claim 24, wherein the mutating is accomplished by treatment with ethylmethane sulfonate.

32. The method of claim 24, wherein the mutating is accomplished by T-DNA insertion.

33. The method of claim 24, wherein the mutating is accomplished by transposable element insertion.

34. The method of claim 24, wherein the vector comprises SEQ ID NO:1 or SEQ ID NO:3.

35. The method of claim 24, wherein the AOX1a promoter and the gene encoding the reporter protein form a polynucleotide of bases 361 through 3317 of SEQ ID NO:1.

36. A method for identifying the nucleic acid sequence of a gene encoding a protein that participates in a signal transduction pathway between branched chain amino acid biosynthetic pathways and nuclear gene expression in *Arabidopsis thaliana* comprising:

(a) transforming the *Arabidopsis thaliana* with a vector, the vector comprising a gene that encodes a luciferase protein operably linked to an *Arabidopsis thaliana* AOX1a promoter consisting essentially of a nucleic acid sequence of SEQ ID NO:4 or the complement thereof;

(b) identifying a transgenic *Arabidopsis thaliana* from step a that increases the expression of luciferase when subjected to a stimulus relative to the basal level of endogenous expression of the gene;

(c) mutating the transgenic *Arabidopsis thaliana* identified in step b;

(d) selecting a mutant transgenic *Arabidopsis thaliana* from step c, wherein the mutant *Arabidopsis thaliana* exhibits altered expression of the luciferase gene relative to an unmutagenized *Arabidopsis thaliana*;

(e) determining the nucleic acid sequence of the gene that encodes the protein that participates in the signal transduction pathway in the mutant *Arabidopsis thaliana* from step d.

37. The method of claim 36, wherein the mutating is accomplished by treatment with ethylmethane sulfonate.

38. The method of claim 36, wherein the mutating is accomplished by T-DNA insertion.

39. The method of claim 36, wherein the mutating is accomplished by transposable element insertion.

40. The method of claim 36, wherein the vector comprises SEQ ID NO:1 or SEQ ID NO:3.

41. The method of claim 36, wherein the AOX1a promoter and the gene encoding the reporter protein form a polynucleotide of bases 361 through 3317 of SEQ ID NO:1.

42. The method of claim 36, wherein the stimulus is metabolic perturbation.

* * * * *